United States Patent
Nabatova-Gabain et al.

(10) Patent No.: US 7,196,793 B2
(45) Date of Patent: Mar. 27, 2007

(54) METHOD FOR ANALYZING THIN-FILM LAYER STRUCTURE USING SPECTROSCOPIC ELLIPSOMETER

(75) Inventors: Nataliya Nabatova-Gabain, Tokyo (JP); Yoko Wasai, Nagoya (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 10/488,596

(22) PCT Filed: Sep. 6, 2002

(86) PCT No.: PCT/JP02/09080

§ 371 (c)(1),
(2), (4) Date: Aug. 25, 2004

(87) PCT Pub. No.: WO03/023373

PCT Pub. Date: Mar. 20, 2003

(65) Prior Publication Data

US 2004/0265477 A1    Dec. 30, 2004

(30) Foreign Application Priority Data

Sep. 6, 2001 (JP) ............... 2001-270668
Apr. 12, 2002 (JP) ............... 2002-110710
Sep. 2, 2002 (JP) ............... 2002-256538

(51) Int. Cl.
*G01J 4/00* (2006.01)

(52) U.S. Cl. .................................... 356/369

(58) Field of Classification Search ........ 356/364–369, 356/630, 438
See application file for complete search history.

(56) References Cited

U.S. PATENT DOCUMENTS

4,999,509 A    3/1991    Wada et al.

(Continued)

FOREIGN PATENT DOCUMENTS

EP          827192 A2          3/1998

(Continued)

OTHER PUBLICATIONS

J. F. Elman et al., "Characterization of Biaxially-Stretched Plastic Films By Generalized Ellipsometry," Thin Solid Films 313-314, (1998), pp. 814-818.

(Continued)

*Primary Examiner*—Gregory J. Toatley, Jr.
*Assistant Examiner*—Isiaka O. Akanbi
(74) *Attorney, Agent, or Firm*—Venable LLP; Michael A. Sartori

(57) ABSTRACT

With extremely-thin-film and thin-film measurement, models are formed based upon a combination of film thickness, optical constants obtained using the dispersion formula, incident angle, etc., and the model and measured spectrums are fit by BLMC for a single layer of a structure with a certain number of iterations, obtaining information regarding the single layer. With thin-film multi-layer-structure measurement, models are formed for multiple layers of a thin-film multi-layer structure likewise, and fit by BLMC or EBLMC, obtaining information regarding the thin-film multi-layer structure. In either measurement, light is cast onto a thin film on a substrate to be measured while changing the wavelength as a parameter in order to obtain the spectrums $\psi_E(\lambda_i)$ and $\Delta_E(\lambda_i)$ for each wavelength $\lambda_i$, representing the change in polarization between the incident and reflected light. The measured spectrums are fit, obtaining the best model. The results are confirmed and stored, as necessary.

34 Claims, 15 Drawing Sheets

U.S. PATENT DOCUMENTS

| | | | |
|---|---|---|---|
| 5,754,296 A * | 5/1998 | Law | 356/369 |
| 5,889,592 A | 3/1999 | Zawaideh | |
| 5,953,446 A | 9/1999 | Opsal et al. | |
| 5,999,267 A * | 12/1999 | Zawaideh | 356/630 |
| 6,002,485 A * | 12/1999 | Masao | 356/369 |
| 6,268,916 B1 * | 7/2001 | Lee et al. | 356/369 |
| 6,278,519 B1 | 8/2001 | Rosencwaig et al. | |
| 6,297,880 B1 * | 10/2001 | Rosencwaig et al. | 356/369 |
| 6,320,657 B1 * | 11/2001 | Aspnes et al. | 356/369 |
| 6,532,076 B1 | 3/2003 | Sidorowich | |
| 6,597,463 B1 * | 7/2003 | Singh et al. | 356/630 |

FOREIGN PATENT DOCUMENTS

| | | |
|---|---|---|
| EP | 1406080 A | 4/2004 |
| JP | 1-123135 A | 5/1989 |
| JP | 11-40635 A | 2/1999 |

OTHER PUBLICATIONS

John A. Woollam et al., "Overview of Variable Angle Spectroscopic Ellipsometry (VASE), Part 1: Basic Theory And Typical Applications," Critical Reviews, vol. CR72, Optical metrology, pp. 3-28, Jul. 18, 1999.

S. A. Alterovitz et al., "Multiple Minima in the Ellipsometric Error Function," Thin Solid Films 313-314, 1998, pp. 124-127.

B. A. Tirri et al., "Spectroellipsometric Characterization of Inhomogenous Films," SPIE vol. 794, 1987, pp. 253-261.

J. G. Webster, Editor, "Ellipsometry, Variable Angle Spectroscopic," Wiley Encyclopedia of Electrical and Electronic Engineering, Supplement 1, 2000, pp. 109-117.

J. C. Comfort et al., "Numerical Techniques Useful in the Practice of Ellipsometry," Thin Solid Films 270, 1995, pp. 78-84.

A. A. Khan et al., "Optical Properties of "Diamondlike" Carbon Films: An Ellipsometric Study," Physical Review B, vol. 28, No. 12, 1983, pp. 7229-7235.

K. G. Merkel et al., "Characterization of Multilayer GaAs/AlGaAs Transistor Structures by Variable Angle Spectroscopic Ellipsometry," Japanese Journal of Applied Science, vol. 28, No. 5, 1989, pp. 1118-1123.

R. H. Muller, "Ellipsometry as an in Situ Probe for the Study of Electrode Processes," Techniques for Characterization of Electrodes and Electrochemical Processes, 1991, pp. 124-127.

M. Land et al., "Using Genetic Algorithms with Local Search for Thin Film Metrology," Proceedings of the Seventh International Conference on Genetic Algorithms (ICGA97), 1997, pp. 537-544.

J. A. Woollam et al., "Overview of Variable Angle Spectroscopic Ellipsometry (VASE), Part I: Basic Theory and Typical Applications," Optical Metrology, Society of Photo-Optical Instrumetation Engineers, reprint of Critical Reviews of Optical Science and Technology, vol. CR72, 2000, pp. 3-26.

B. Johs et al., "Overview of Variable Angle Spectroscopic Ellipsometry (VASE), Part II: Advanced Applications," Optical Metrology, Society of Photo-Optical Instrumetation Engineers, reprint of Critical Reviews of Optical Science and Technology, vol. CR72, 2000, pp. 29-58.

J. M. Leng et al., "Simultaneous Measurement of Six Layers in a Silicon on Insulator ilm Stack Using Spectrophotometry and Beam Profile Reflectrometry," J. Appl. Phys. 81 (8), 1997, pp. 3570-3578.

G. E. Jellison, Jr., "Use of the Biased Estimator in the Interpretation of Spectroscopic Ellipsometry Data," Applied Optics, vol. 30, No. 23, 1991, pp. 3354-3360.

G. H. Bu-Abbud et al., "Parameter Correlation and Precisionin Multiple-Angel Ellipsometry," Applied Optics, vol. 20, No. 17, 1981, pp. 3020-3026.

Y. Cong et al., "Optical Characterization of a Four-Medium Thin Film Structure by Real Time Spectroscopic Ellipsometry: Amorphous Carbon on Tantalum," Applied Optics, vol. 30, No. 19, 1991, pp. 2692-2703.

S. Bosch et al., "Effective Dielectric Function of Mixtures of Three or More Materials: A Numerical Procedure for Computations," Surface Science 453, 2000, pp. 9-17.

R.M.A. Azzam et al., "Ellipsometry and Polzrized Light", Elsevier (1977), pp. 270-340.

N. Yoshinori et al., "Full Automatic Spectroscopic Ellipsometer UT-300 Part 1 System Configuration", Sep. 2000, pp. 18-21.

N. Blayo, Ph.D., "Full Automatic Spectroscopic Ellipsometer UT-300, (Part 1) Basic Principles of Ellipsometry and PEM", Sep. 2000.

N. Blayo, Ph.D., "Full Automatic Spectroscopic Ellipsometer UT-300, (Part 2) Basic Principles of Ellipometry and PEM", Sep. 2000, pp. 22-25.

S.Hirakawa, "(Part 3) Example of the Multilayer Analysis", Sep. 2000, pp. 26-30.

Atago Bussan Co., Ltd. "Modeling in Ellipsometrical Measurements - General", Oct. 31, 2000, pp. 34-37.

D. Bhattacharyya et al., "Spectroscopic Ellipsometry of Multilayer Dielectric Coatings," Vacuum, Pergamon Press, GB, vol. 60, No. 4, Mar. 2001 (2001-03), pp. 419-424.

G.Xiang et al., "Studies of Metallic Multilayer Structures, Optical Properties, and Oxidation Using In Situ Spectroscopic Ellipsometry," Journal of Physics, New York, NY, US, vol. 16, No. 2, Mar. 1998 (1998-03), pp. 429-435.

* cited by examiner

METHOD FOR ANALYZING THIN-FILM LAYER STRUCTURE USING SPECTROSCOPIC ELLIPSOMETER

BACKGROUND OF THE INVENTION

1. Field of the Invention

The present invention relates to a measurement method for performing precise measurement of the film thickness, the optical constants, and the like, for a thin film or an extremely-thin-film on a substrate, by analyzing the data acquired from a spectroscopic ellipsometer using the Best Local Minimum Calculation (which will be referred to as "BLMC" hereafter).

Furthermore, the present invention relates to an analysis method for an extremely-thin-film-double-layer structure by analyzing the data acquired from a spectroscopic ellipsometer using the Extended Best Local Minimum Calculation (which will be referred to as "EBLMC" hereafter).

Furthermore, the present invention relates to a analysis method for a thin-film-multi-layer structure using a spectroscopic ellipsometer. More specifically, the present invention relates to an analysis method for analyzing the data, which has been acquired from a spectroscopic ellipsometer, with regard to a multi-layer structure formed of unknown materials using the EBLMC as analysis means.

2. Description of the Related Art (Description of General Background with Regard to a Spectroscopic Ellipsometer)

In general, a spectroscopic ellipsometer has a function wherein polarized light is cast onto a sample so as to measure the change in polarization between the incident light and the reflected light. Making an assumption that the complex refractive indexes of the ambient atmosphere and the substrate are known, the film thickness (d) and the complex refractive index ($N=n-ik$) can be calculated based upon the change in polarization between the incident light and the reflected light (in a case of analyzing a sample formed of only the substrate, the complex refractive index ($N_0$) is calculated). The change in polarization ($\rho$) is represented by $\rho = \tan(\psi)\exp(i\Delta)$, and is dependent upon parameters such as the wavelength ($\lambda$), the incident angle ($\phi$), the film thickness, the complex refractive indexes of the film, the substrate, the ambient atmosphere, and the like. The film thickness and the complex refractive index of the film of interest are obtained based upon the measured change in polarization and the following relationship.

$$(d, n, k) = F(\rho) = F(\psi(\lambda,\phi), \Delta(\lambda,\phi))$$

In case of single wavelength ellipsometer, if the incident angle is fixed, only two independent variables of three unknown values of (d, n, k) can be measured, and accordingly, there is the need to fix one of d, n, and k as a known value. Note that in the event that measurement is made with multiple incident angles, the number of measured variables increases, even if the single wavelength ellipsometer is used. However, measured pairs of ($\Psi(\phi_1), \Delta(\phi_1)$) corresponding to different incidence angles ($\phi$), are partly correlated, leading to difficulties in obtaining precise values of d, n, and k.

The measured spectrum measured by spectroscopic ellipsometer ($\Psi_E(\lambda_i), \Delta_E(\lambda_i)$), which represents the change in polarization due to reflection from single-layer or multi-layer thin films formed on a substrate, includes all information with regard to n and k of the aforementioned substrate, and d, n, and k of each layer. However, the single combination of the information with regard to n and k of the aforementioned substrate, and d, n, and k of each layer, cannot be simply extracted from the aforementioned measured spectra (excluding the case of semi-infinite substrate). In general, the method for extracting of the aforementioned single combination is referred to as "spectroscopic ellipsometry data analysis". During this analysis, modeling is performed using the information with regard to n and k of the aforementioned substrate, and d, n, and k of each layer. The information regarding to n and k of the substrate and each layer included in the model is obtained from reference data (known table data), a dispersion formula, or optical constants of a single-layer thin film from a similar material.

The dispersion formula represents the wavelength-dependency of the dielectric constant of the material, wherein the dielectric constant $\epsilon(\lambda)$ can be determined in the optical range between near infrared light and ultraviolet light based upon the atomic structure of the material. Known examples of dispersion formulas include a formula based on classical physics (a harmonic oscillator), a formula based on quantum mechanics, an empirical formula, and the like, which generally include two or more parameters. The model is applied to the measured data by adjusting all the unknown values (thickness of each layer, parameters of the dispersion formula, volume fractions of material's components, or the like) included in the aforementioned model. This processing is referred to as "fitting", wherein the thickness, parameters of dispersion formula, the volume fractions, and the like, of each layer are obtained. The complex dielectric constant $\epsilon(\lambda)$ of the material can be calculated from the parameters of the dispersion formula, based upon the fitting results. The relation between the complex dielectric constant of the material and the complex refractive index is represented by the following expression.

$$\epsilon(\lambda) = N^2(\lambda)$$

Now, brief description will be made regarding fitting operation frequently employed in methods according to the present invention.

(Description Regarding the Fitting Figure of Merit $\chi^2$)

With the set of N pairs of measured (experimental) data as Exp(i=1, 2, and so on through N), and with the set of N pairs of the data calculated using the model as Mod(i=1, 2, and so on through N), making assumption that error of measurement follows normal distribution, and with the standard deviation as $\sigma i$, the mean square error ($\chi^2$) is represented by the expression $$\chi^2 = [1/(2N-P)] \sum_{i=1}^{N} (\text{Exp}_i - \text{Mod}_i)^2 / \sigma_i^2$$

wherein P represents the number of the parameters. The aforementioned expression indicates that the smaller $\chi^2$ is, the better the model matches the measured results. Accordingly, the best model can be selected from multiple models by selecting the model having the smallest $\chi^2$.

In a case of a sample wherein a single film is formed on a substrate, the change in polarization is proportional to the phase angle ($\beta$)×the cross-section area of the beam. The phase angle ($\beta$)(Film Phase Thickness) is represented by the following expression.

$$\beta = 2\pi(d/\lambda)(N^2 - N_A^2 \sin^2 \phi)^{1/2}$$

Making an assumption that the beam's cross section is constant, the change in polarization can be expressed Change in polarization ∝ Film thickness (d)×f($N_A$, $N_0$, N, φ)

Here, $N_A$ denotes the complex refractive index of the ambient atmosphere, $N_0$ denotes the complex refractive index of the substrate, N denotes the complex refractive index of the film, and φ denotes the incident angle. Note that in general, $N_A$ denotes the complex refractive index of the air, and accordingly, $N_A$ will be omitted hereafter. In the event that both the film thickness (d) and the complex refractive index (N) are small, the change in the phase angle (β) exhibits small value, in some cases, leading to difficulty in measurement. Specifically, in this case, the film thickness (d) and the complex refractive index (N) become strongly correlated.

Analysis of an extremely-thin-film-multi-layer structure is even more problematic, because the strong correlation between the film thickness (d) and the complex refractive index (N) may occur for each layer. In this case, it is difficult to obtain d, n, and k, for each film based upon the measurement results ($\psi_E(\lambda_i)$, $\Delta_E(\lambda_i)$) which represent the change in polarization between the incident light and the reflected light.

Furthermore, as can be understood from the aforementioned expression, the precision of the incident angle affects the change in polarization. Accordingly, a method for obtaining a precise incident angle is necessary. That is to say, determination of the precise incident angle allows the precise determination of the change in the polarization of reflected light.

In the present invention, Effective Medium Theory (EMT) is used to calculate the effective dielectric function of materials, those dielectric function's wavelength dependence is difficult or impossible to express, using only one dispersion formula.

In general, the effective dielectric constant (ε) of the host material which contains N number of inclusions (guest materials), each inclusion is big enough to possess it's own dielectric constant, is represented by the expression $$(\varepsilon - \varepsilon_h)/(\varepsilon + k\varepsilon_h) = \sum_{j=1}^{N} f_j(\varepsilon_j - \varepsilon_h)/(\varepsilon_j + k\varepsilon_h)$$

wherein $\varepsilon_h$ represents the dielectric constant of the host material, $\varepsilon_j$ represents the dielectric constant of the j-th guest material, and k represents a screening factor. Now, let us consider a case in which one cannot distinguish between the host material and the guest material, i.e., a case that materials of comparable amount have been mixed. In this case, approximation can be made wherein the dielectric constant of the host material and the effective dielectric constant of mixed material are the same $\varepsilon_h = \varepsilon$, therefore $\varepsilon_h$ in the aforementioned expression is replaced by the effective dielectric constant ε. The aforementioned approximation is called "Bruggeman Effective Medium Approximation", which will be simply referred to as "EMA" in this specification hereafter. Using the EMA, the effective dielectric constant ε of a material, wherein three spherical components a, b, and c have been uniformly mixed, is obtained by the expression $$f_a(\varepsilon_a-\varepsilon)/(\varepsilon_a+2\varepsilon)+f_b(\varepsilon_b-\varepsilon)/(\varepsilon_b+2\varepsilon)+f_c(\varepsilon_c-\varepsilon)/(\varepsilon_c+2\varepsilon)=0$$

wherein ε represents the effective dielectric constant which is to be obtained, $\varepsilon_a$, $\varepsilon_b$, and $\varepsilon_c$, represent the dielectric constants of the spherical components a, b, and c, respectively, and $f_a$, $f_b$, and $f_c$, represent the volume fraction of the corresponding components. Volume fraction will be referred to as "Vf", hereafter. Note that $f_a+f_b+f_c=1$.

Effective Medium Approximation (EMA) is applicable, if the separate regions (components) of mixed material are small compared to the wavelength of light. EMA is used to model thin film on substrate, if this film is either microscopically inhomogeneous or discontinuous or formed by several physically mixed materials.

Now, description will be made regarding a case that the materials a, b, and c have been mixed. In this case, EMA is used to calculate the dielectric constant of the mixed layer from the volume fractions of each component and the dielectric constants of corresponding materials a, b and c. Dielectric constant of each component can be determined by either reference data or dispersion formula. Assuming the mixed layer thickness, model can be built and fitted to the measured data.

The calculation methods which are referred to as "BLMC (Best Local Minimum Calculation)" and "EBLMC (Extended Best Local Minimum Calculation) are frequently used in the analysis method according to the present invention. In this specification, these calculation methods will be referred to the abbreviations of "BLMC" and "EBLMC" hereafter.

BLMC is used for analyzing a single-layer structure. In the analysis using the BLMC, fitting is made with a predetermined procedure while adjusting the initial values of predetermined parameters within a certain range, so as to obtain the best results.

EBLMC is used for analyzing a multi-layer structure. In the analysis using the EBLMC, BLMC is repeated for a film of interest while maintaining the predetermined kinds of parameters of the other films to multiple values at and around the medians thereof, and the best results are determined as the results obtained with the EBLMC.

SUMMARY OF THE INVENTION

It is a first object of the present invention to provide an extremely-thin-film measurement method and a thin-film measurement method for analyzing the data acquired from a spectroscopic ellipsometer, wherein fitting is made with regard to the measured data acquired from the spectroscopic ellipsometer and simulation spectrum calculated from a model employing a combination of the film thickness, the complex refractive index of the film, and the like, using the BLMC, thereby determining an extremely-thin-film structure and a thin-film structure.

It is another object of the present invention to provide an extremely-thin-film-double-layer-structure analysis method for determining an extremely-thin-film double structure from the measured data acquired from a spectroscopic ellipsometer, wherein fitting is made with regard to the measured data acquired from the spectroscopic ellipsometer and simulation spectrum calculated from a model employing a combination of the film thickness, the complex refractive index of the film, and the like, using the EBLMC.

It is a further object of the present invention to provide a thin-film-multi-layer-structure analysis method for determining a thin-film-multi-layer structure from the measured data acquired from a spectroscopic ellipsometer, wherein fitting is made with regard to the measured data acquired from the spectroscopic ellipsometer and simulation spectrum calculated from a model employing a combination of the film thickness, the complex refractive index of the film, and the like, using the EBLMC.

In order to achieve the aforementioned first object, the present invention provides an extremely-thin-film measurement and thin-film measurement method for analyzing spectroscopic data acquired from a spectroscopic ellipsometer using best-local-minimum-calculation (BLMC), which comprises a spectrum measurement step wherein incident light is cast onto a thin film on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; a step for assuming the complex refractive index ($N_0$, ($n_0$, $k_0$)) of the substrate, the complex refractive index (N, (n, k)) of the film, based upon the dispersion formula, a plurality of film thicknesses (d±mΔd) within a plausible range, and a plurality of incident angles (φ±mΔφ) within a plausible range; a step for performing fitting for the parameters of the dispersion formula (DSP) based upon combinations of the incident angle and the film thickness; an analyzing step 1A for selecting fitting results ($DSP_{best}$) obtained based upon a model formed of a combination of the film thickness ($d_{best}$) and the incident angle ($\phi_{best}$), which exhibits the minimal difference between the $\psi_M(\lambda_i)$ and $\Delta_M(\lambda_i)$ obtained by the fitting and the measured $\psi_E(\lambda_i)$ and $\Delta_E(\lambda_i)$; an analyzing step 2A for performing fitting for the film thickness ($d_{best}$) and the dispersion formula ($DSP_{best}$) with the incident angle ($\phi_{best}$) obtained in the analyzing step 1A being fixed.

In the analyzing step 1A and analyzing step 2A, the mean square error ($\chi^2$) may be calculated from the measured values and the fitting results for each model, and the fitting results which exhibit the minimal mean square error ($\chi^2$) are selected.

In order to achieve the aforementioned first object, the present invention provides an extremely-thin-film measurement and thin-film measurement method for analyzing spectroscopic data acquired from a spectroscopic ellipsometer using best-local-minimum-calculation (BLMC), which comprises a spectrum measurement step wherein incident light is cast onto a thin film on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; a step for forming models of the film structure, wherein a thin film on a substrate is formed with microscopic non-uniformity, or is formed of a mixture of several materials, with the complex refractive index ($N_0$, ($n_0$, $k_0$)) of the substrate and the complex refractive index (N, (n, k)) of the film, assumed based upon several dispersion formulas or reference data, which are used for Effective Medium Approximation (EMA); a step for assuming a plurality of film thicknesses (d±mΔd) within a plausible range, a plurality of volume fractions (Vf±mΔVf) within a plausible range obtained based upon the dispersion formulas which have been employed in forming the models, and a plurality of incident angles (φ±mΔφ) within a plausible range; a step for performing fitting for the parameters of the dispersion formula (DSP) based upon combinations of the incident angle, the film thickness, and the volume fraction; an analyzing step 1A for selecting fitting results ($DSP_{best}$) obtained based upon a model formed of a combination of the film thickness ($d_{best}$), the incident angle ($\phi_{best}$), and the volume fraction ($Vf_{best}$), which exhibits the minimal difference between the $\psi_M(\lambda_i)$ and $\Delta_M(\lambda_i)$ obtained by the fitting and the measured $\psi_E(\lambda_i)$ and $\Delta_E(\lambda_i)$; and an analyzing step 2A for performing fitting for the film thickness ($d_{best}$), the volume fraction ($Vf_{best}$), and the dispersion formula ($DSP_{best}$) with the incident angle ($\phi_{best}$) obtained in the analyzing step 1A being fixed.

In order to achieve the aforementioned first object, the present invention provides an extremely-thin-film measurement and thin-film measurement method for analyzing spectroscopic data acquired from a spectroscopic ellipsometer using best-local-minimum-calculation (BLMC), which comprises a spectrum measurement step wherein incident light is cast onto a thin film on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; a step for assuming a plurality of measurement conditions ($Z_j$) in a plausible range and performing processing from the second step of the aforementioned extremely-thin-film measurement and thin-film measurement method for forming models of a film structure, to the second step, for each ($Z_j$); and an analyzing step 3A for selecting fitting results, of which the parameters of the dispersion formula and the volume fraction are within predetermined ranges, exhibiting the minimal mean square error ($\chi^2$), from the fitting results obtained based upon the plurality of measurement conditions ($Z_j$).

In order to achieve the aforementioned second object, the present invention provides an extremely-thin-film double-layer-structure measurement method for analyzing spectroscopic data acquired from a spectroscopic ellipsometer, wherein at first the spectroscopic spectrums are generally obtained by measuring the extremely-thin-film double-layer-structure using the spectroscopic ellipsometer.

New analysis method is generally formed with three analyzing stages. In the analyzing stage 1, the initial values are determined by selecting the plurality of models, which is assumed to match an actual sample. In the analyzing stage 2, EBLMC is performed based upon the initial values obtained in the analyzing stage 1. In the analyzing stage 3, the final fitting is performed and the results are confirmed and stored, as necessary.

In order to achieve the aforementioned second object, the present invention provides an extremely-thin-film double-layer-structure measurement method for analyzing spectroscopic data acquired from a spectroscopic ellipsometer, which comprises a spectrum measurement stage wherein incident light is cast onto an extremely-thin-film double-layer structure on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; an analyzing stage 1B which includes an analyzing step 1B-1 for forming several models of the extremely-thin-film double-layer structure on the substrate based upon the complex refractive index ($N_0$, ($n_0$, $k_0$)) of the substrate, the complex refractive indexes ($N_1$, ($n_1$, $k_1$)) and ($N_2$, ($n_2$, $k_2$)) of materials (Mat 1, Mat 2) of the thin films in plausible ranges, and the film thicknesses ($d_1$, $d_2$) in plausible ranges; an analyzing step 1B-2 for performing fitting for the measured spectrums for each model; and an analyzing step 1B-3 for selecting fitting results ($d_{1(best)}$, $d_{2(best)}$) obtained based upon a model which exhibits the minimal mean square error ($\chi^2$), or a model with the film thicknesses being within predetermined ranges, which exhibits the minimal mean square error ($\chi^2$), from the fitting results obtained based upon the several models; an analyzing stage 2B which includes an analyzing step 2B-1 for setting initial values of a new model to the fitting results obtained in the analyzing stage 1B; an analyzing step 2B-2 for performing fitting for multiple models with a film-thickness combination as a parameter around and at the film-thickness combination ($d_{1(best)}$, $d_{2(best)}$) serving as the median, using BLMC; and an analyzing step 2B-3 for selecting a model which exhibits the minimal mean square error ($\chi^2$), or a model with the film thicknesses, the parameters of the dispersion formula, and the incident angle, being within predetermined ranges, which exhibits the minimal mean square error ($\chi^2$); an analyzing stage 3B which includes an analyzing step 3B-1 for performing the final fitting based upon the fitting results obtained in the analyzing stage 2B; an analyzing step 3B-2 for confirming the fitting results obtained in the analyzing step 3B-1; and an analyzing step 3B-3 for storing the obtained fitting results.

In the analyzing step 2B-2, fitting may be performed using BLMC for materials formed of the double-layer structure in order of uncertainty of the optical constants thereof.

The aforementioned extremely-thin-film double-layer-structure measurement method may further comprise a step for forming multiple models with the film thickness obtained in the analyzing step 1B-3, of which the optical constants are more reliable than the other, as a parameter around and at the film thickness obtained in a range of a few percents to a few ten percents; a step for performing BLMC described in the analyzing steps 2B-2 and 2B-3 for the other layer for each model.

In order to achieve the aforementioned second object, the present invention provides an extremely-thin-film double-layer-structure measurement method for analyzing spectroscopic data acquired from a spectroscopic ellipsometer, which comprises a spectrum measurement stage wherein incident light is cast onto an extremely-thin-film double-layer-structure on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; an analyzing stage 1B which includes an analyzing step 1B-1 for forming several models of one of the first and second layers, which is formed with non-uniformity or non-continuity, or is formed of a mixture of several materials, with the complex refractive index ($N_0$, ($n_0$, $k_0$)) of the substrate thereof, the complex refractive indexes ($N_1$, ($n_1$, $k_1$)) and ($N_2$, ($n_2$, $k_2$)) of the materials (Mat 1, Mat 2) forming the thin films in plausible ranges, the volume fractions ($Vf_1$, $Vf_2$) in plausible ranges, and the film thicknesses ($d_1$, $d_2$) in plausible ranges, using Effective Medium Approximation (EMA); an analyzing step 1B-2 for performing fitting for the measured spectrums for each model; and an analyzing step 1B-3 for selecting fitting results ($d_{1(best)}$, $d_{2(best)}$, $Vf_{(best)}$) obtained based upon a model which exhibits the minimal mean square error ($\chi^2$), or a model with the film thicknesses and the volume fractions being within predetermined ranges, which exhibits the minimal mean square error ($\chi^2$), from the fitting results obtained based upon the several models; an analyzing stage 2B which includes an analyzing step 2B-1 for forming new models with the initial values based upon the fitting results obtained in the analyzing stage 1B, with the film thickness, wherein the corresponding parameters of the dispersion formula are less known than the other, as a parameter around the value obtained the analyzing step 1B-3 in a range of ($d_1 \pm m\Delta d_1$) or ($d_2 \pm m\Delta d_2$), with the film thickness of the other layer as a parameter around the value obtained the analyzing step 1B-3 in a range of ($d_2 \pm m\Delta d_2$) or ($d_1 \pm m\Delta d_1$), and with the volume fraction as a parameter around the value obtained the analyzing step 1B-3 in a range of ($Vf \pm m\Delta Vf$); an analyzing step 2B-2 for performing BLMC for the parameters of the layer, wherein the parameters of the dispersion formula are less known than the other, of the models obtained in the analyzing step 2B-1; and an analyzing step 2B-3 for selecting a model which exhibits the minimal mean square error ($\chi^2$), or a model with the film thicknesses, the parameters of the dispersion formula, and the incident angle, being within predetermined ranges, which exhibits the minimal mean square error ($\chi^2$), from the fitting results obtained in the analyzing step 2B-2; an analyzing stage 3B which includes an analyzing step 3B-1 for performing fitting for the film thicknesses of both thin films, the volume fraction, and the parameters of the dispersion formula, or performing fitting for the film thicknesses of both thin films and the volume fraction, based upon the fitting results obtained in the analyzing stage 2B; an analyzing step 3B-2 for confirming the fitting results obtained in the analyzing step 3B-1; and an analyzing step 3B-3 for storing the obtained fitting results.

The aforementioned extremely-thin-film double-layer-structure measurement method may further comprise a spectrum measurement stage wherein incident light is cast onto an extremely-thin-film double-layer-structure on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; a step for assuming a plurality of measurement conditions (Zi) in a plausible range and performing processing from the analyzing stage 1B or analyzing step 2B-1 through 2B-3 of the aforementioned extremely-thin-film double-layer-structure measurement method for each assumed measurement condition (Zi); and an analyzing step 1B-4 or 2B-4 for selecting fitting results, which exhibit the minimal mean square error ($\chi^2$), or the parameters of the dispersion formula, and the volume fraction, are within a predetermined range, and which exhibit the minimal mean square error ($\chi^2$) which are selected from the fitting results obtained in the analyzing step.

In each of the steps for selecting the results which exhibit the least difference, described in the analyzing stage 1B, 2B, and 3B, the mean square error ($\chi^2$) may be obtained between the fitting results and the measured values, and the fitting results which exhibit the minimal mean square error ($\chi^2$), or the fitting results, of which the film thicknesses, the parameters of the dispersion formula, the volume fraction, and the change in the incident angle, are within predetermined ranges, and which exhibit the minimal mean square error ($\chi^2$), are selected.

In order to achieve the aforementioned third object, the present invention provides a thin-film triple-layer-structure measurement method for analyzing spectroscopic data acquired from a spectroscopic ellipsometer, which comprises a spectroscopic measurement phase for obtaining measured data using a spectroscopic ellipsometer; an analyzing phase 1C for forming an initial model of a thin-film triple-layer-structure; an analyzing phase 2C which includes an analyzing stage 2C-1 for determining unknown parameters of the layer of interest forming the thin-film triple-layer-structure, using EBLMC; and an analyzing stage 2C-2 for determining parameters of the other layers with the parameters determined in the analyzing stage 2C-1 being fixed, using EBLMC.

In order to achieve the aforementioned third object, the present invention provides a thin-film triple-layer-structure measurement method for analyzing spectroscopic data acquired from a spectroscopic ellipsometer, which comprises a spectroscopic measurement phase for obtaining measured data using a spectroscopic ellipsometer; an analyzing phase 1C for forming an initial model of a thin-film triple-layer-structure; an analyzing phase 2C which includes an analyzing stage 2C-1 for determining unknown parameters of the layer of interest forming the thin-film triple-layer-structure, using EBLMC; and an analyzing stage 2C-2 for determining parameters of the other layers with the parameters determined in the analyzing stage 2C-1 being fixed, using EBLMC; an analyzing phase 3C which includes an analyzing stage 3C-1 for performing the final fitting for the model obtained in the analyzing phase 2C; an analyzing stage 3C-2 for confirming the fitting results obtained in the analyzing stage 3C-1; and an analyzing stage 3C-3 for storing the fitting results obtained in the analyzing stage 3C-2.

In order to achieve the aforementioned third object, the present invention provides a thin-film n-layer-structure measurement method for analyzing spectroscopic data acquired from a spectroscopic ellipsometer, which comprises a spectroscopic measurement phase for obtaining measured data using a spectroscopic ellipsometer; an analyzing phase 1C for forming an initial model of a thin-film n-layer-structure; and an analyzing phase 2C for determining unknown parameters of the layer of interest forming the n-layer structure based upon the initial model which represents the thin-film n-layer-structure, using EBLMC.

In order to achieve the aforementioned third object, thin-film n-layer-structure measurement method for analyzing spectroscopic data acquired from a spectroscopic ellipsometer, which comprises a spectroscopic measurement phase for obtaining measured data using a spectroscopic ellipsometer; an analyzing phase 1C for forming an initial model of a thin-film n-layer-structure; an analyzing phase 2C for determining unknown parameters of the layer of interest forming the n-layer structure based upon the initial model, using EBLMC; an analyzing phase 3C which includes an analyzing stage 3C-1 for performing the final fitting for the model obtained in the analyzing phase 2C; an analyzing stage 3C-2 for confirming the fitting results obtained in the analyzing stage 3C-1; and an analyzing stage 3C-3 for storing the fitting results obtained in the analyzing stage 3C-2.

Analysis may be made with unknown parameters as the film thicknesses, the optical constants of unknown materials or the volume fractions.

The spectroscopic measurement phase may include a spectrum measurement step wherein incident light is cast onto a thin-film triple-layer structure or a thin-film multi-layer structure on a substrate which is to be measured while changing the wavelength of the incident light as a parameter in order to obtain the $\psi_E$ and $\Delta_E$ spectrums, i.e., the $\psi_E(\lambda_i)$ and $\Delta_E(\lambda_i)$ for each wavelength $\lambda_i$, which represent the change in polarization between the incident light and the reflected light; and a storage step for storing the data obtained in the measured step.

In the analyzing phase 1C, the single Best First Approximation Model (which will be referred to as "BFAM" hereafter) may be selected from a plurality of models by fitting, or a model is assumed based upon known data, as the initial model, and wherein in a case of employing the BFAM, the analyzing phase 1C which includes an analyzing step 1C-1 for forming a plurality of models within a plausible range; an analyzing step 1C-2 for performing fitting with regard to the film thicknesses, the volume fractions, and the incident angles, based upon the plurality of models; and an analyzing step 1C-3 for selecting a model which exhibit the minimal mean square error ($\chi^2$), or a model, of which the film thicknesses, the volume fractions, and the incident angles, are within predetermined ranges, and which exhibit the minimal mean square error ($\chi^2$), from the fitting results obtained in the analyzing step 1C-2.

The analyzing stage 2C-1 may include an analyzing step 2C-1-1 for replacing the optical constants of the layer of interest with a single dispersion formula, which is the least known in the thin-film triple-layer structure or thin-film n-layer structure, in the determined initial model; an analyzing step 2C-1-2 for forming a plurality of models based upon the initial model with the film thicknesses, the volume fractions, or the like, of desired layers other than the layer of interest (the number of layers is 1 through (n−1)), as parameters; performing EBLMC for the layer of interest based upon each model; an analyzing step 2C-1-3 for selecting a model which exhibit the minimal mean square error ($\chi^2$), or a model, of which the film thicknesses, the volume fractions, the parameters of the dispersion formula, and the incident angle, are within predetermined ranges, and which exhibit the minimal mean square error ($\chi^2$), from the fitting results using EBLMC, obtained in the analyzing step 2C-1-2.

In each of analyzing stages 2C-2 through 2C-t, the same steps as the analyzing step 2C-1-1 through analyzing step 2C-1-3 described in the aforementioned thin-film triple-layer-structure measurement or thin-film multi-layer-structure measurement method may be performed, making an assumption that the optical constants of the layer of interest obtained in the previous stage are almost known.

In the analyzing phase 2C, EBLMC may be performed for the materials forming the triple-layer structure or n-layer structure in order of uncertainty of the optical constants of the materials, and wherein the EBLMC is performed for at least one to t times, regardless of the number of the layers in the structure.

In the analyzing phase 2C, in the event that the fitting results with the minimal mean square error ($\chi^2$) do not exhibit the film thicknesses, the parameters of the dispersion formula, the volume fractions, and the incident angle, within predetermined ranges, the analyzing phase 2C may be repeated with a certain number of iterations.

In the analyzing phase 3C, the final fitting may be performed for desired parameters of the model obtained the analyzing phase 2C, confirmation is made for the fitting results obtained in the final fitting, and the fitting results are stored.

In the event that confirmation is made in the analyzing step 3C-2 that the fitting results with the minimal mean square error ($\chi^2$) obtained in the analyzing step 3C-1 may not be within predetermined ranges, the flow returns to the analyzing phase 1C, and analysis is made again.

The analyzing stage 2C-1 may include an analyzing step 2C-1-1 wherein in the event that the layer of interest cannot be represented by a single dispersion formula in the same way as the aforementioned thin-film triple-layer-structure measurement or thin-film multi-layer-structure measurement method, Effective Medium Approximation (EMA) is performed making an assumption that the layer of interest is formed of a mixture of several materials, and at least one material forming the layer of interest is represented by a dispersion formula; an analyzing step 2C-1-2 for forming multiple models with film thicknesses or volume fractions of desired layers 1 through (n−1) (n denotes the number of layers of the structure) other than the layer of interest, as parameters and performing EBLMC for the layer of interest for each model while changing the volume fraction thereof as a parameter.

The aforementioned thin-film triple-layer-structure measurement or thin-film multi-layer-structure measurement method may further comprise a spectroscopic measurement phase wherein incident light is cast onto a triple-layer-structure or multi-layer-structure on a substrate which is to be measured while changing the wavelength of the incident light as a parameter in order to obtain the $\psi_E$ and $\Delta_E$ spectra, i.e., the $\psi_E(\lambda_i)$ and $\Delta_E(\lambda_i)$ for each wavelength $\lambda_i$, which represent the change in polarization between the incident light and the reflected light; an analyzing step for assuming a plurality of measurement conditions (Zi) in a plausible range and performing processing from the analyzing step 1C or analyzing step 1C-1 through 2C-t-3 for each assumed measurement condition (Zi); and an analyzing step 1C-4 or 2C-t-4 for selecting fitting results, which exhibit the minimal mean square error ($\chi^2$), or the parameters of the dispersion formula, the volume fraction, and the incident angle, are within a predetermined range, and which exhibit the minimal mean square error ($\chi^2$) which are selected from the fitting results obtained in the analyzing step.

In each of the steps for selecting the results which exhibit the least difference, described in the analyzing phases 1C, 2C, and 3C, the mean square error ($\chi^2$) may be obtained between the fitting results and the measured values, and the fitting results which exhibit the minimal mean square error ($\chi^2$), or the fitting results, of which the film thicknesses, the parameters of the dispersion formula, the volume fraction, and the change in the incident angle, are within predetermined ranges, and which exhibit the minimal mean square error ($\chi^2$), are selected.

As described above in detail, the present invention provides an excellent analysis method for analyzing a thin-film layer structure based upon spectroscopic data acquired from a spectroscopic ellipsometer, thereby enabling precise measurement of the properties of a thin film such as the film thickness, the volume fraction, and the optical constants thereof in the semiconductor manufacturing field.

DESCRIPTION OF THE PREFERRED EMBODIMENTS (Description Regarding an Extremely-thin-film Measurement Method and a Thin-film Measurement Method According to Embodiments of the Present Invention)

Description will be made regarding embodiments according to the present invention with reference to the drawings and the like.

Figure 1:
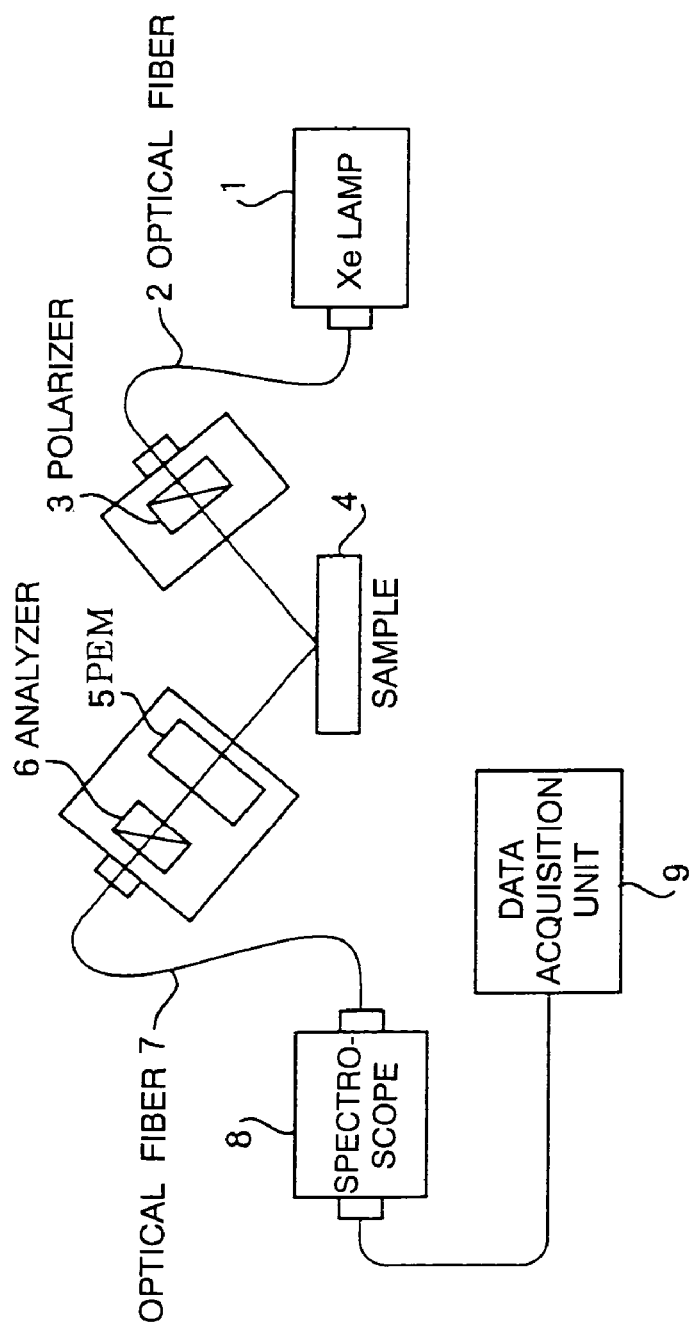
FIG. 1 is a block diagram which shows a configuration of a spectroscopic ellipsometer for acquiring spectroscopic measured data, employed in step 10 in an extremely-thin-film measurement method and a thin-film measurement method according to the present invention.

FIG. 1 is a block diagram which shows a configuration of an ellipsometer used in an extremely-thin-film measurement method and a thin film measurement method according to the present invention. The spectroscopic ellipsometer shown in the block diagram performs a spectroscopic measurement step 10 to obtain the measured spectroscopic data described later.

A Xe lamp 1 is a so-called white light source for emitting light containing a great number of wavelength components. The light emitted from the Xe lamp 1 is introduced to a polarizer 3 through an optical fiber 2. The light polarized by the polarizer 3 is cast onto the surface of a sample 4 which is to be measured with a predetermined incident angle (e.g., $\phi=75°$). The reflected light from the sample 4 is introduced to an analyzer 6 through a photo-elastic modulator (PEM) 5. The reflected light is subjected to phase modulation with a frequency of 50 kHz by the photo-elastic modulator (PEM) 5. As a result the polarization of the reflected light, which is originated from the linearly polarized incident light, will change periodically from linearly to elliptically. Accordingly, $\Psi$ and $\Delta$ can be determined within several msec. The output from the analyzer 6 is connected to a spectroscope 8 through an optical fiber 7. The output data from the spectroscope 8 is acquired by a data acquisition unit 9, whereby the spectroscopic measurement step 10 to obtain the measured spectroscopic data ends. Note that the PEM 5 may be situated in front of the polarizer 3 or the analyzer 6.

It is assumed that the model is preferably modified by adjusting the incident angle $\phi_0$, rather than fixing the model to a model with the nominal incident angle $\phi_0$ shown in FIG. 1, due to slight non-uniformity of the surface of the sample. That is to say, it is assumed that the aforementioned $\psi_E$ and $\Delta_E$ have been measured under an incident angle slightly deviated from the nominal incident angle.

With the actual thin-film measurement method using the aforementioned spectroscopic ellipsometer, analysis is made as follows. First, with the nominal incident angle used in the aforementioned $\psi_E$, $\Delta_E$ spectrum measurement step as $\phi_0$, in the aforementioned $\psi_M$, $\Delta_M$ model simulation spectrum calculation step, the simulation spectrums $\psi_{M0}(\lambda_i)$ and $\Delta_{M0}(\lambda_i)$ are calculated with the nominal incident angle $\phi_0$, and the simulation spectrums $\psi_{Mk}(\lambda_i)$ and $\Delta_{Mk}(\lambda_i)$ are calculated with an incident angle $\phi_k$ near the nominal incident angle $\phi_0$. Subsequently, the above-described model-simulation spectrums are calculated in block 21, and are compared to the $\psi_E(\lambda_i)$ and $\Delta_E(\lambda_i)$ acquired from the spectroscopic ellipsometer.

Figure 2:
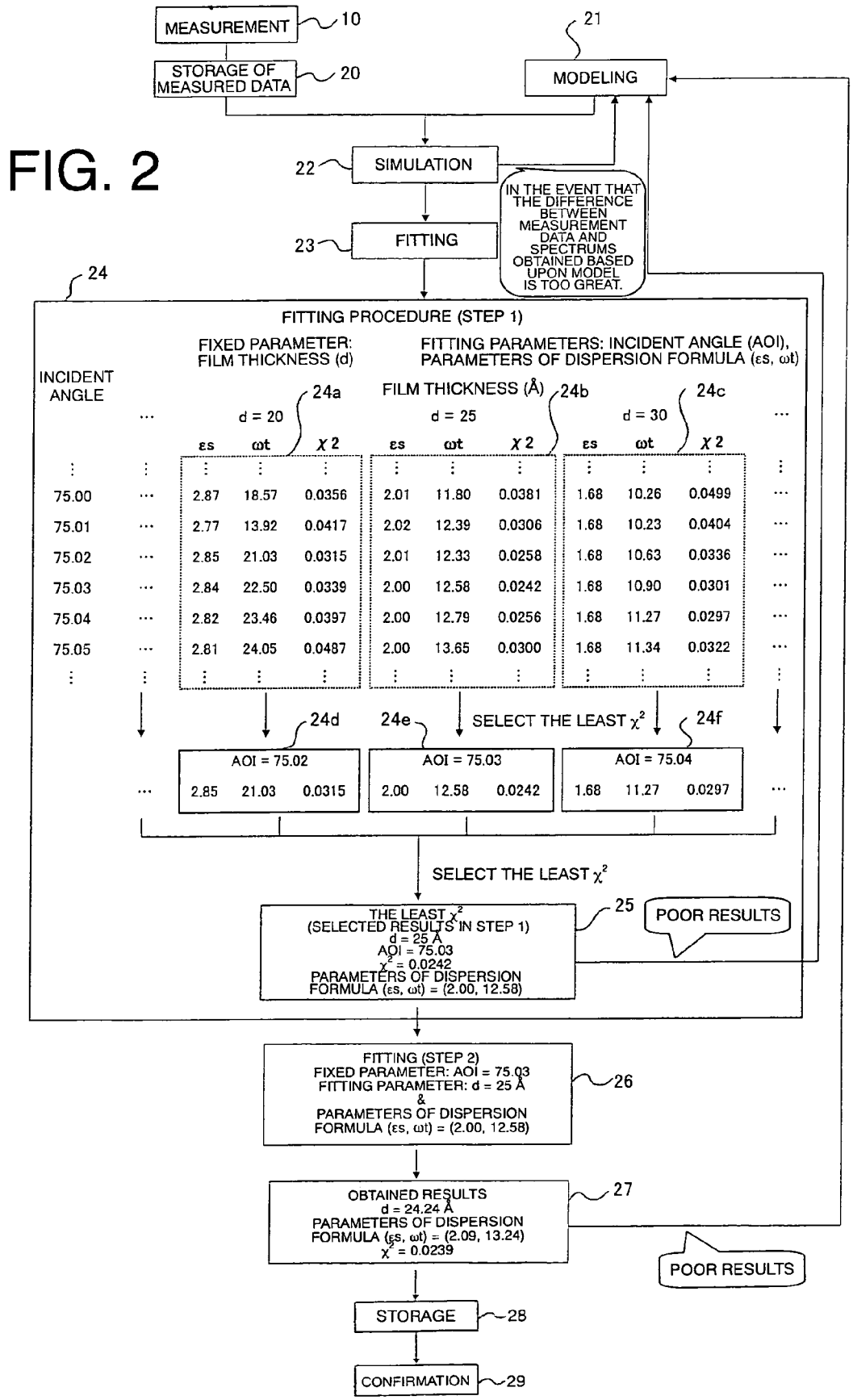
FIG. 2 is a flowchart for describing an extremely-thin-film measurement method and a thin-film measurement method according to the present invention.

FIG. 2 is a flowchart which shows a thin-film measurement method according to a first embodiment of the present invention.

(Block 10)

Measurement is made using the apparatus shown in FIG. 1.

(Block 20)

In this step, the spectroscopic measurement data is processed into the data in a format which can be compared with the simulated results. More specifically, the spectroscopic measurement data acquired in the aforementioned acquisition block 10 for acquiring the spectroscopic measurement data is converted into the data in the format of $\psi_E(\lambda_i)$ and $\Delta_E(\lambda_i)$, and the converted data is stored.

(Block 21)

In block 21, modeling is made for the sample which is to be measured with spectroscopic ellipsometry. Specifically, modeling is made for the sample which is to be measured, based upon the conditions at the time of the manufacturing process and the like. Note that modeling is made for the same sample as in block 20.

The aforementioned modeling is made with multiple film thicknesses within a plausible range (d±mΔd), with the dispersion formula assumed based upon the material forming the layer on the substrate, and with multiple incident angles within a plausible range ($\phi$±mΔ$\phi$).

With the present embodiment, a great number of models are formed with a Si substrate, with a first $SiO_x$ layer thickness of 20 Å, 25 Å, and 30 Å, and with the measurement incident angle of 75.00° to 75.05° in increments of 0.01°.

(Block 22)

In the processing shown in block 22, the $\psi_M$ and $\Delta_M$ calculated based upon the aforementioned models, and the measurement data $\psi_E$ and $\Delta_E$ are displayed.

(Block 23)

Fitting is made for each model.

(Block 24)

Fitting results for the dispersion formula are displayed for each model. The fitting results with regard to the parameters ($\epsilon_s$, $\omega_t$) of the dispersion formula (DSP) calculated with the $SiO_x$ film thicknesses of 20 Å, 25 Å, and 30 Å, are shown in blocks 24a, 24b, and 24c, with the incident angle as a parameter.

(Block 25)

In block 25, a single combination of the incident angle and the film thickness is selected. Note that the selection will be referred to as "first-stage fitting" hereafter. In this example, the first-stage fitting is made as follows. First, let us consider a case of the fitting results with the film thickness of 20 Å shown in block 24a. In this case, the fitting results obtained with the incident angle of 75.02° exhibit the minimal $\chi^2$ value of 0.0315 (see block 24d). Next, in a case of the fitting results with the film thickness of 25 Å shown in block 24b, the fitting results obtained with the incident angle of 75.03° exhibit the minimal $\chi^2$ value of 0.0242 (see block 24e). On the other hand, in a case of the fitting results with the film thickness of 30 Å shown in block 24c, the fitting results obtained with the incident angle of 75.04° exhibit the minimal $\chi^2$ value of 0.0297 (see the block 24f). In this case, the model ($\phi_{best}$=75.03°, $d_{best}$=25 Å) shown in block 24e which exhibits the minimal $\chi^2$ value of 0.0242 is selected from these three models.

(Block 26)

In block 26, fitting is made with regard to the aforementioned film thickness ($d_{best}$) and the parameters ($\epsilon_s$, $\omega_t$) of the dispersion formula with the incident angle ($\phi_{best}$) selected in the aforementioned first-stage fitting as a fixed value. In this example, fitting is made with regard to the film thickness ($d_{best}$) and the parameters of the dispersion formula ($\epsilon_s$, $\omega_t$), with the film thickness ($d_{best}$) of 25 Å as an initial value, with the parameters of the dispersion formula of ($\epsilon_s$, $\omega_t$)= (2.00, 12.58) as initial values, and with the incident angle ($\phi_{best}$) of 75.03° as a fixed value. Thus, second-stage fitting is completed.

(Block 27)

The fitting results in the aforementioned second-stage fitting are shown in block 27. In this example, the film thickness d of 24.24 Å, and the parameters ($\epsilon_s$, $\omega_t$) of the dispersion formula of (2.09, 13.24) are obtained as the final fitting results.

(Block 28)

The data calculated in the step described in the aforementioned block 27 is stored.

(Block 29)

Confirmation is made that the aforementioned stored data is plausible from the perspective of physics. The fitting results obtained in the aforementioned first-stage or second-stage fitting step may be unrealistic from both the physical and empirical perspective. In this case, determination is made that flawed models have been used, and modification of models, such as addition or changing of the material forming the models, is made, and fitting is made again using the modified models. The confirmation is made in block 22, block 25, and block 27, and in the event that determination is made that the fitting results are impossible from the perspective of physics, the flow returns to block 21, as shown in FIG. 2.

Next, description will be made regarding an implemented example of an extremely-thin-film measurement method and a thin-film measurement method for measuring a film on a substrate, having a non-uniform or non-continuous structure, or formed of a mixture of multiple materials, based upon the data acquired from the spectroscopic ellipsometer using the BLMC.

In the implemented example, measurement is made for a film formed of $SiO_2$ and $SiN_x$ (mixture layer SiON) on a Si substrate.

(Measurement Step)

In the measurement step, incident light is cast onto the aforementioned thin film (mixture layer of $SiO_2$ and $SiN_x$) on the substrate which is to be measured while changing the wavelength of the incident light as a parameter, in order to obtain measured spectrums $\psi_E(\lambda_i)$ and $\Delta_E(\lambda_i)$, which represent the change in polarization between the incident light and the reflected light, for each wavelength $\lambda_i$. Measurement is made using the same measurement apparatus as described above.

(Step for Forming Models)

In this step, models are formed for representing a mixture layer formed of $SiO_2$ and $SiN_x$, serving as a thin film on the substrate.

First, the Si substrate serves as a bulk, and accordingly, $(N_0, (n_0, k_0))$ of the aforementioned Si substrate can be easily determined. On the other hand, (d, N, (n, k)) of the thin film on the substrate are determined using the Effective Medium Approximation (EMA), and accordingly, models for the thin film are assumed based upon several dispersion formulae or reference data.

Now, let us say that the initial values of the model of the thin film are determined as follows.

Volume fraction (Vf): $SiO_2$ (30%)+$SiN_x$ (70%)

Thickness (d): 20 Å

Furthermore, multiple film thicknesses are determined within a plausible range (d±mΔd). In the same way, multiple volume fractions and multiple incident angles are determined within a plausible ranges (Vf±mΔ Vf) and (φ±mΔφ), respectively.

(Fitting Step for the Parameters of the Dispersion Formula)

Fitting is made with regard to the parameters ($\epsilon_s$, $\omega_t$) of the dispersion formula based upon the aforementioned combinations of the incident angle, the film thickness, and the volume fraction.

(Step for First Selection)

The difference between the spectrums $\psi_M(\lambda_i)$ and $\Delta_M(\lambda_i)$ obtained by the aforementioned fitting and the aforementioned measured spectrums $\psi_E(\lambda_i)$ and $\Delta_E(\lambda_i)$ is calculated for each model. The fitting result ($DSP_{best}$) corresponding to the model with the film thickness ($d_{best}$), the incident angle ($\phi_{best}$), and the volume fraction ($Vf_{best}$), which exhibits the minimal difference is determined.

(Step for Second Selection)

Fitting is made with regard to the film thickness ($d_{best}$), the volume fraction ($Vf_{best}$), and the dispersion formula ($DSP_{best}$), with the incident angle ($\phi_{best}$) determined in the aforementioned step for first selection as a fixed value. As a result, in this example, the following results are obtained.

Volume fractions (Vf): $SiO_2$ (57.1%)+$SiN_x$ (42.9%)

film thickness (d): 32.5 Å

(Step for Modification of the Model in the Event that Determination is Made that the Data Obtained by Fitting is Impossible from the Perspective of Physics)

In some cases, the fitting results obtained in the aforementioned step for first selection or second selection, may be unrealistic from both the physical and empirical perspective. In this case, determination is made that fitting has been made using flawed models, and modification of the models, such as change or addition of the material forming the models, is made so as to make fitting again. The modification of the models and the fitting using the modified model are repeated until plausible fitting results are obtained. Note that while the step for confirmation is necessary in practice, the aforementioned step is not an essential component in the present invention, and an arrangement may be made wherein the step for confirmation is omitted.

(Description Regarding an Implemented Example of an Analysis Method for an Extremely-thin-film Double-layer Structure)

Description will be made regarding an implemented example of an analysis method according to the present invention for analyzing an extremely-thin-film double-layer structure based upon the data acquired from a spectroscopic ellipsometer, with reference to the drawings and the like.

Figure 3:
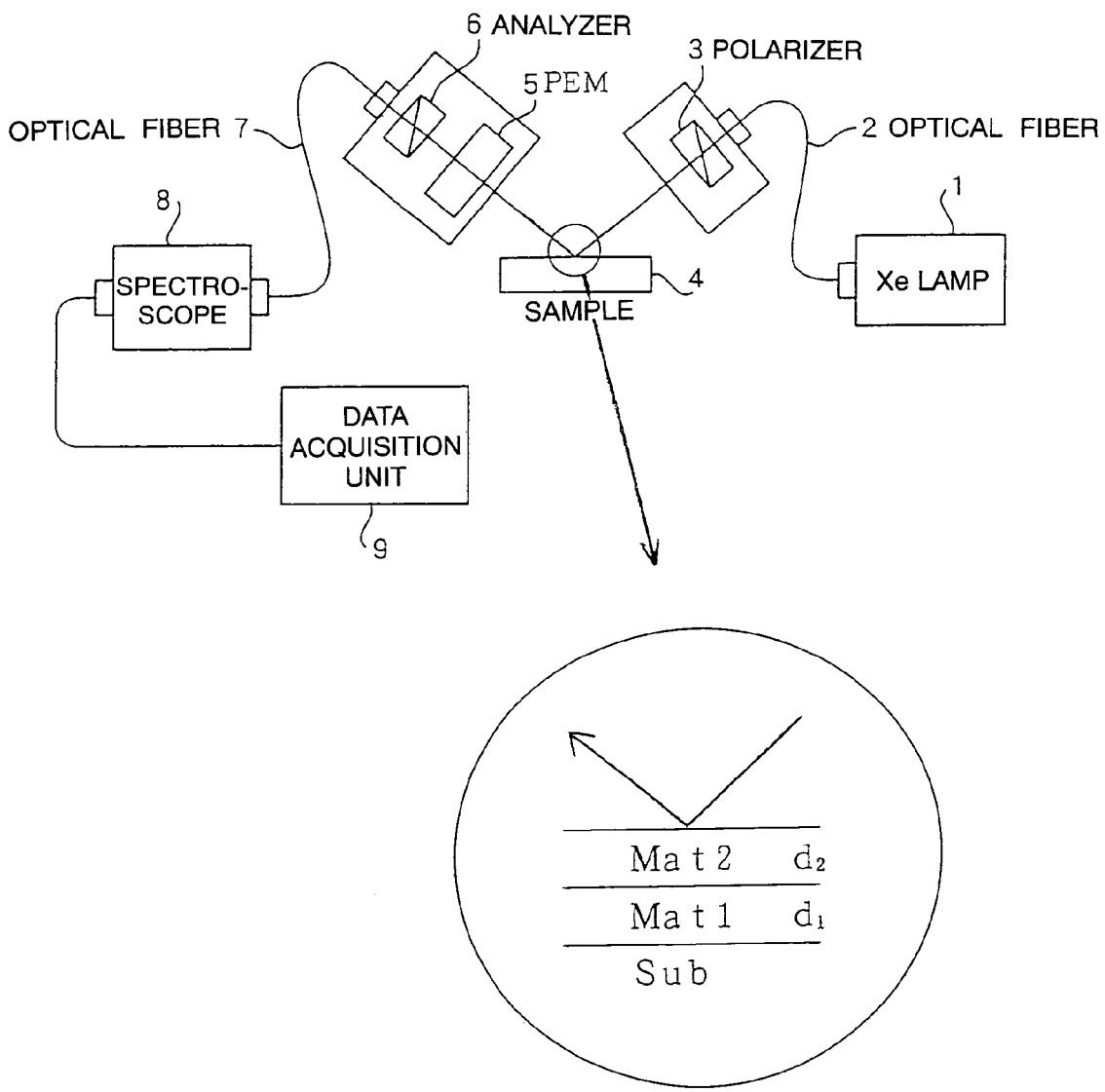
FIG. 3 is a schematic diagram which shows a configuration of an ellipsometer employed in an extremely-thin-film double-layer-structure measurement method according to the present invention, wherein a part of a sample which is to be measured is enlarged.

FIG. 3 is a diagram which shows a configuration of the ellipsometer used in the analysis method for an extremely-thin-film double-layer structure. Note that an enlarged part of a sample 4, which is to be measured, is shown in FIG. 3.

The processing shown in the step for acquiring the spectroscopic measurement data described later is performed using the spectroscopic ellipsometer shown in FIG. 3. First, description will be made regarding the measurement apparatus. A Xe lamp 1 is a so-called white light source for emitting light containing a great number of wavelength components. The light emitted from the Xe lamp 1 is introduced to a polarizer 3 through an optical fiber 2. The light polarized by the polarizer 3 is cast onto the surface of a sample 4 which is to be measured with a predetermined incident angle (e.g., φ=75°). Note that the sample 4 is a measurement sample wherein two thin-film layers are formed on a substrate described later.

The reflected light from the sample 4 is introduced to an analyzer 6 through a photo-elastic modulator (PEM) 5. The reflected light is subjected to phase modulation with a frequency of 50 kHz by the photo-elastic modulator (PEM) 5. As a result the polarization of the reflected light, which is originated from the linearly polarized incident light, will change periodically from linearly to elliptically. Accordingly, Ψ and Δ can be determined within several msec. The output from the analyzer 6 is connected to a spectroscope 8 through an optical fiber 7. The output data from the spectroscope 8 is acquired by a data acquisition unit 9, whereby the spectroscopic measurement step to obtain the measured spectroscopic data ends. Note that the PEM 5 may be situated in front of the polarizer 3 or the analyzer 6.

Figure 4:
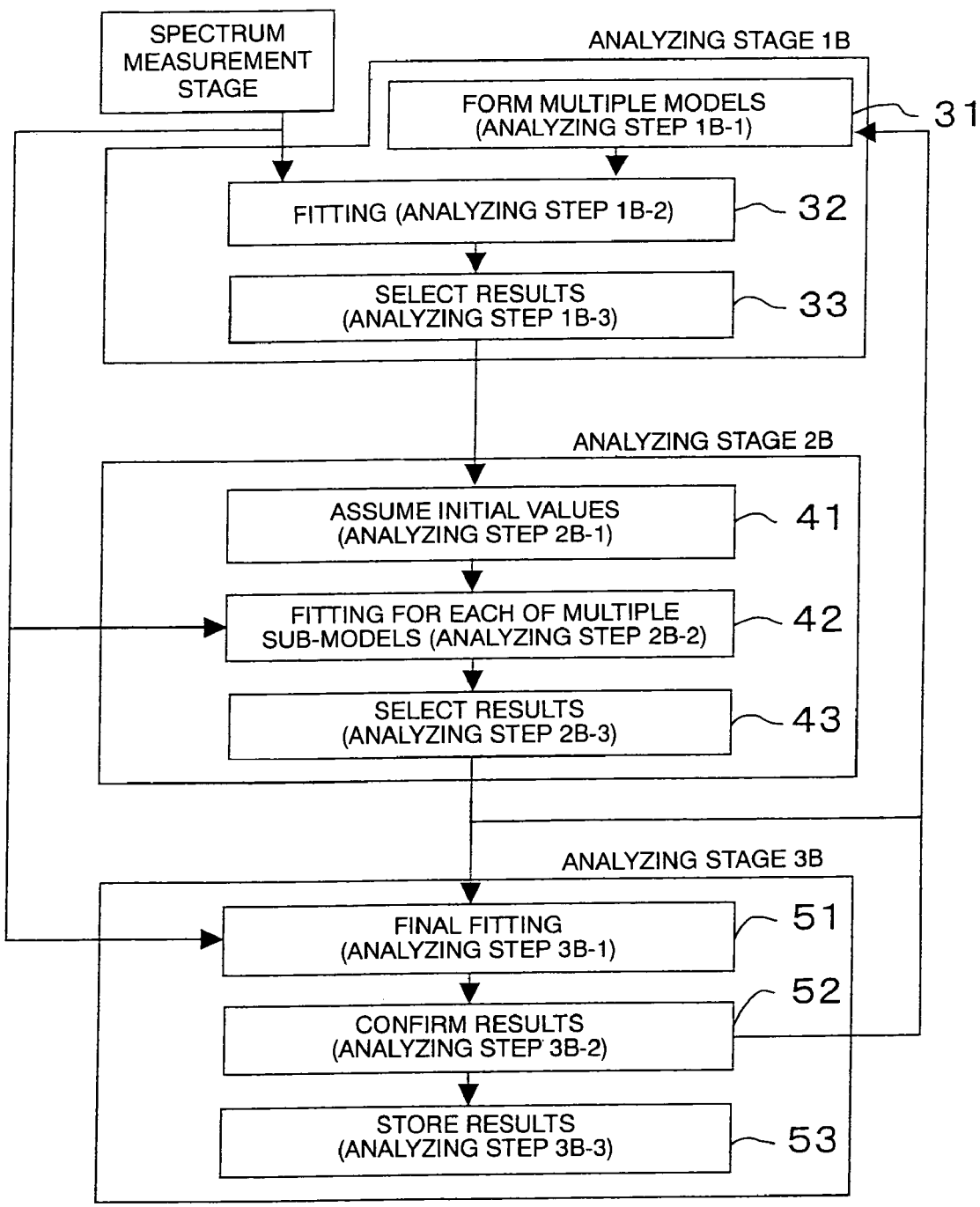
FIG. 4 is a flowchart which shows an extremely-thin-film double-layer-structure measurement method according to an embodiment of the present invention.
Figure 5:
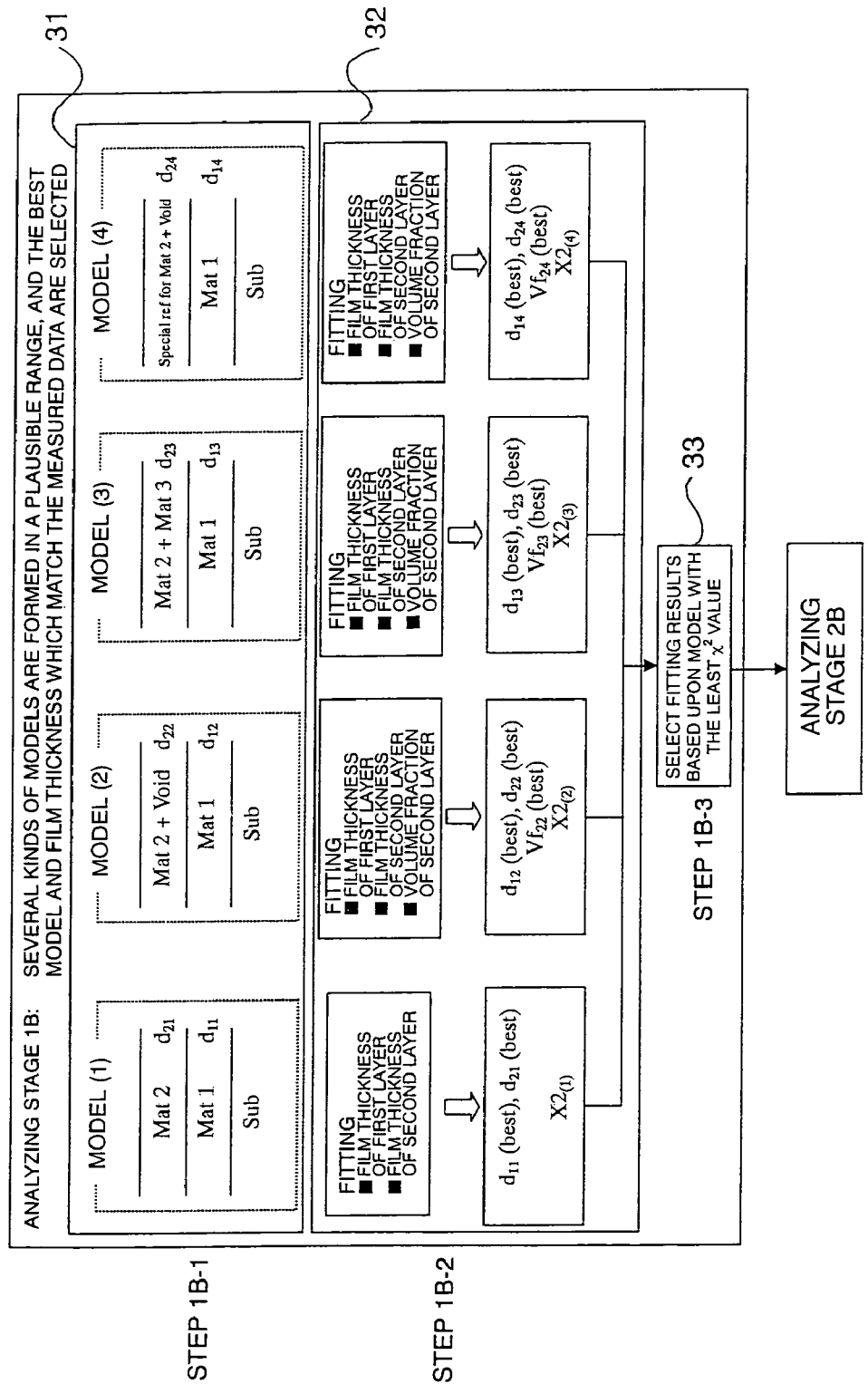
FIG. 5 is an explanatory diagram for describing an analyzing stage 1B of the aforementioned embodiment in detail.
Figure 6:
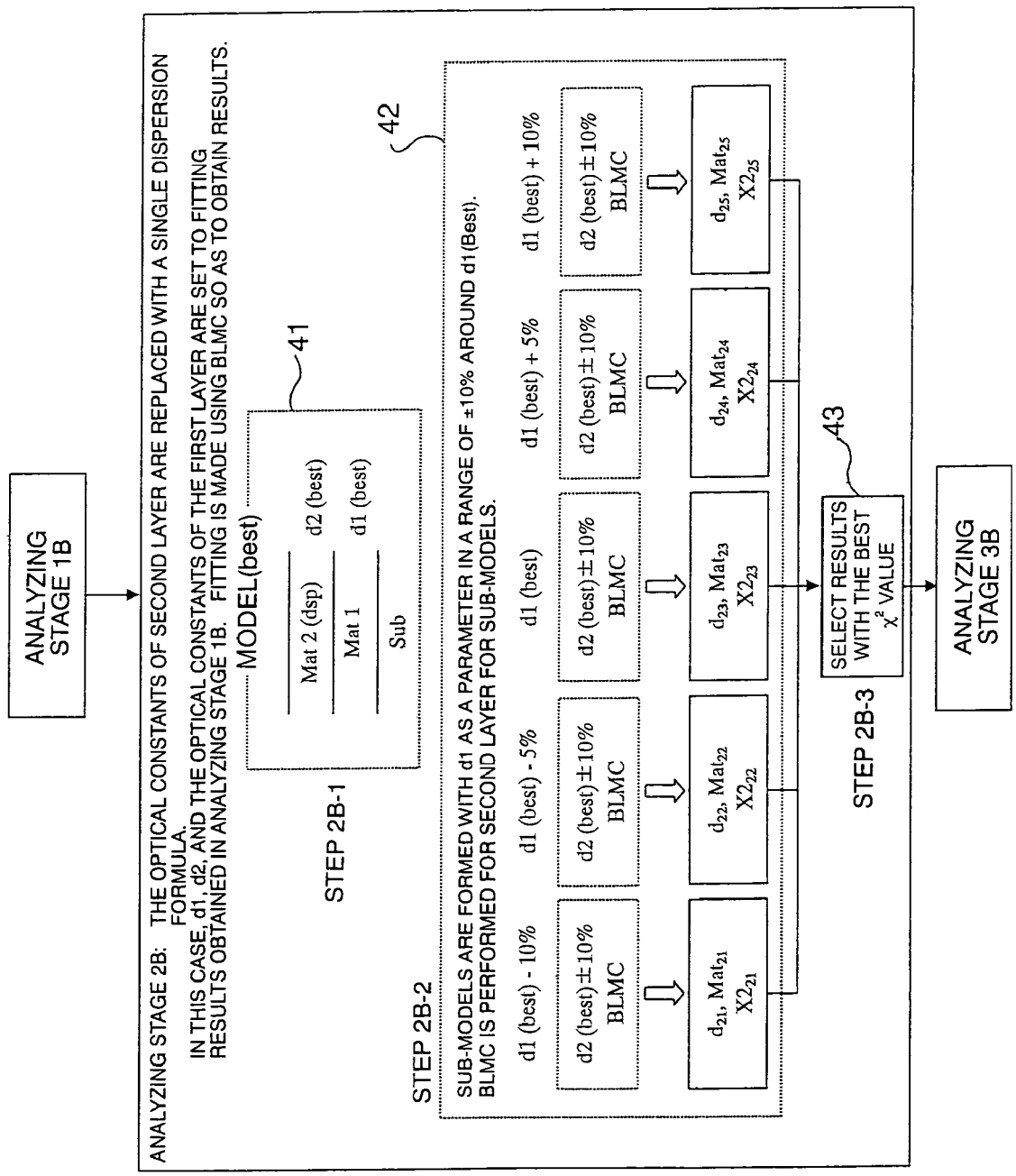
FIG. 6 is an explanatory diagram for describing an analyzing stage 2B of the aforementioned embodiment in detail.
Figure 7:
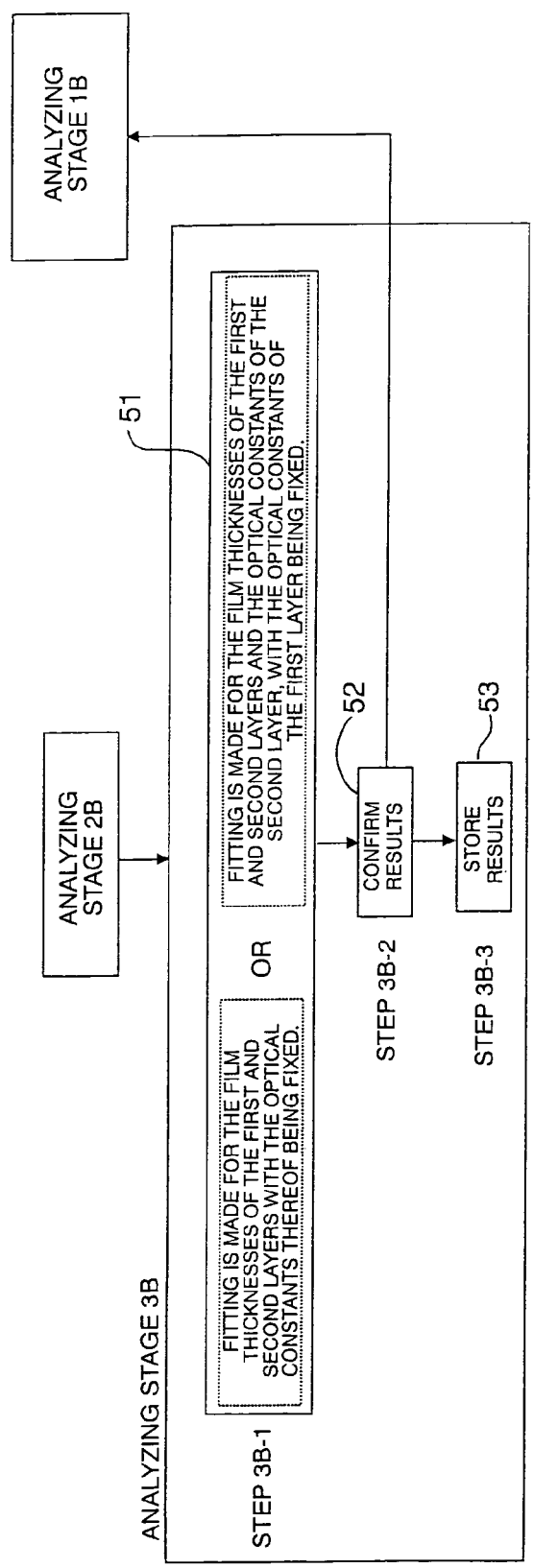
FIG. 7 is an explanatory diagram for describing an analyzing stage 3B of the aforementioned embodiment in detail.

FIG. 4 is a flowchart which shows an extremely-thin-film double-layer-structure measurement method according to an embodiment of the present invention. FIG. 5 is an explanatory diagram for describing an analyzing stage 1B of the aforementioned embodiment in detail. FIG. 6 is an explanatory diagram for describing an analyzing stage 2B of the aforementioned embodiment in detail. FIG. 7 is an explanatory diagram for describing an analyzing stage 3B of the aforementioned embodiment in detail.

Now, reference characters are listed as follows.

(Definition of the Reference Characters)

Sub: substrate (with known optical constants, which serves as a bulk)

Mat: material forming a thin film (optical constants of the material)

$Mat_{ij}$: material used in the j'th model forming the i'th layer (optical constants of the i'th layer's material)

$d_i$: film thickness of the i'th layer $d_{i(best)}$: film thickness of the i'th layer obtained by fitting $d_{ij}$: film thickness of the i'th layer in the j'th model $d_{ij(best)}$: film thickness of the i'th layer in the j'th model obtained by fitting $\chi^2$: mean square error ($\chi^2$)

$\chi^2_{(j)}$: mean square error ($\chi^2$) at the time of fitting based upon the j'th model Void: material with n=1, and k=0

$Vf_{(ij)}$: volume fraction of the material in the i'th layer in the j'th model $Vf_{(ij)(best)}$: volume fraction of the material in the i'th layer in the j'th model obtained by fitting (Measurement Stage: Measurement)

Measurement is made using the apparatus shown in FIG. 3. In the measurement stage, incident light is cast onto a thin-film double-layer structure on a substrate (see the enlarged view in FIG. 3) serving as a sample 4, which is to be measured, while changing the wavelength of the incident light as a parameter, in order to obtain measured spectrums $\psi_E(\lambda_i)$ and $\Delta_E(\lambda_i)$, which represent the change in polarization between the incident light and the reflected light for each wavelength $\lambda_i$.

(Measurement Stage: Data Storage)

The data measured in the aforementioned stage is stored as the comparative data (see FIG. 4).

(Analyzing Step 1B-1)

In this step, several models are formed based upon the ($N_0$, ($n_0$, $k_0$)) of the substrate, the plausible complex refractive indexes ($N_1$, ($n_1$, $k_1$)) and ($N_2$, ($n_2$, $k_2$)) of the materials (Mat 1, Mat 2) forming the thin films, and the film thicknesses ($d_1$, $d_2$).

In this implemented example, let us say that four models (1) through (4) are formed as follows. The schematic configuration of these models are shown in block 31 in FIG. 5.

The model (1) represents a film structure wherein a first layer (formed of a material having the optical constants of the Mat 1, with the film thickness of $d_{11}$) and a second layer (formed of a material having the optical constants of the Mat 2, with the film thickness of $d_{21}$) are formed on a substrate (Sub).

The model (2) represents a film structure wherein a first layer (formed of a material having the optical constants of the Mat 1, with the film thickness of $d_{12}$) and a second layer (formed of a material having the optical constants of the Mat 2, and Void, with predetermined volume fraction and with the film thickness of $d_{22}$) are formed on a substrate (Sub). Note that the aforementioned Void represents a material having the refractivity of cavities, which is 1.

The model (3) represents a film structure wherein a first layer (formed of a material having the optical constants of the Mat 1, with the film thickness of $d_{13}$) and a second layer (formed of a material having the optical constants of the Mat 2, and a material having the optical constants of the Mat 3, with the film thickness of $d_{23}$) are formed on a substrate (Sub). Note that the aforementioned second layer 2 is formed of a mixture of the material 2 and material 3 with a predetermined volume fraction.

The model (4) represents a film structure wherein a first layer (formed of a material having the optical constants of the Mat 1, with the film thickness of $d_{14}$) and a second layer (formed of a material having generally the same optical constants as the Mat 2, mixed with the Voids, with the film thickness of $d_{24}$) are formed on a substrate (Sub).

Here, the second layers in the aforementioned models (2) through (4) can be approximated as a uniform film using the Effective Medium Approximation (EMA), thereby obtaining optical constants of the approximated uniform film based upon the volume fractions set to the second layer thereof. Note that the above-described four models are formed, making an assumption that the optical constants of the material forming the substrate (Sub) are known, the optical constants of the first layer are generally known, the optical constants of the second layer, the film thickness $d_1$ of the first layer, and the film thickness $d_2$ of the second layer, are unknown (uncertain).

(Analyzing Step 1B-2)

Fitting is performed with regard to each of the four models (1) through (4) formed in the above-described step 1B-1, and the measured data $\psi_E$ and $\Delta_E$ obtained from the above-described measured spectrums. The mean square error values ($\chi^2$) obtained at the time of fitting for the fitting parameters of each model are shown in block 32 in FIG. 5.

During the fitting of the model (1), fitting is performed for the film thickness of $d_{11}$ of the first layer and the film thickness of $d_{21}$ of the second layer, whereby the fitting results $d_{11(best)}$ and $d_{21(best)}$, and the mean square value $\chi^2_{(1)}$, are obtained.

During the fitting of the model (2), fitting is performed for the film thickness of $d_{12}$ of the first layer, the film thickness of $d_{22}$ of the second layer, and the volume fraction of the second layer, whereby the fitting results $d_{12(best)}$, $d_{22(best)}$, $Vf_{22(best)}$, and the mean square value $\chi^2_{(2)}$, are obtained.

During the fitting of the model (3), fitting is performed for the film thickness of $d_{13}$ of the first layer, the film thickness of $d_{23}$ of the second layer, and the volume fraction of the second layer, whereby the fitting results $d_{13(best)}$, $d_{23(best)}$, $Vf_{23(best)}$, and the mean square value $\chi^2_{(3)}$, are obtained.

During the fitting of the model (4), fitting is performed for the film thickness of $d_{14}$ of the first layer, the film thickness of $d_{24}$ of the second layer, and the volume fraction of the second layer, whereby the fitting results $d_{14(best)}$, $d_{24(best)}$, $Vf_{24(best)}$, and the mean square value $\chi^2_{(4)}$, are obtained.

(Analyzing Step 1B-3)

In this step shown in block 33 in FIG. 5, the fitting results corresponding to the model which exhibits the minimal $\chi^2$ value, or the fitting results, of which the film thicknesses and the volume fraction are in predetermined ranges, corresponding to the model which exhibits the minimal $\chi^2$ value, are selected from the fitting results obtained in the fitting for the aforementioned multiple models.

(Analyzing Step 2B-1)

A model (initial values) used in the analyzing step 2 is shown in block 41 in FIG. 6. In this example, the optical constants of the Mat 1 are generally known, and accordingly, the optical constants of the Mat 1 used in the analyzing stage 1B are used without change. The optical constants of the material (Mat 2) forming the second layer are unknown, and accordingly, in this case, the dispersion formula is employed. Note that the film thicknesses obtained in the analyzing step 1B-3 are used as the initial values of the film thicknesses (d).

(Analyzing Step 2B-2)

In this step, as shown in block 42 in FIG. 6, five sub-models are formed as follows:

1) A sub-model having the same structure as shown in block 41 in FIG. 6;
2) A sub-model having a structure wherein the film thickness of the first layer $d_{1(best)}$ of the structure shown in block 41 is changed by +10%;
3) A sub-model having a structure wherein the film thickness of the first layer $d_{1(best)}$ of the structure shown in block 41 is changed by +5%;

4) A sub-model having a structure wherein the film thickness of the first layer $d_{1(best)}$ of the structure shown in block 41 is changed by −5%; and
5) A sub-model having a structure wherein the film thickness of the first layer $d_{1(best)}$ of the structure shown in block 41 is changed by −10%.

Subsequently, BLMC is performed for each of the aforementioned five sub-models while changing the film thickness of the second layer ($d_{2(best)}$) within a range of ±10% as a parameter. Thus, the film thickness of the second layer $d_{2j}$, the optical constants thereof $Mat_{2j}$, and the $\chi^2$ value $\chi^2_{(j)}$ are obtained. Note that j represents the index number of each sub-model.

(Analyzing Step 2B-3)

In this step, the fitting results corresponding to the model which exhibits the minimal $\chi^2$ value, or the fitting results, of which the film thicknesses and the parameters of the dispersion formula are in predetermined ranges, corresponding to the model which exhibits the minimal $\chi^2$ value, are selected from the fitting results obtained in the aforementioned step 2B-2 (see the block 43 in FIG. 6). Note that in the event that determination is made that the fitting results are impossible from the perspective of physics, the flow returns to the analyzing stage 1B, and modeling is made again, following which fitting is performed again (step 2B-2).

(Analyzing Step 3B-1)

Fitting is performed for the film thicknesses of the first and second layers with the optical constants of the first layer and second layer being fixed to the results corresponding to the model selected in the above-described analyzing step 2B-3. Alternately, fitting is performed for the film thicknesses of the first and second layers, and the optical constants of the second layer, with the optical constants of the first layer being fixed (see the block 51 in FIG. 7).

(Analyzing Step 3B-2)

Confirmation is made that the film thickness and the parameters of the dispersion formula, which have been obtained as the fitting results exhibiting the minimal $\chi^2$ value in the above-described step 3B-1, are within predetermined ranges (see the block 52 in FIG. 7). Note that in the event that determination is made that the obtained fitting results are impossible from the perspective of physics, the flow returns to the analyzing stage 1B, and modeling is made again, following which fitting is performed again (step 2B-2).

(Analyzing Step 3B-3)

In the event that determination has been made that the obtained fitting results are plausible from the perspective of physics in the above-described step 3B-2, the obtained fitting results are stored (see the block 53 in FIG. 7).

(Implemented Example)

Next, description will be made regarding an implemented example for analyzing a structure wherein the optical constants of the first layer are generally known, and the optical constants of the second layer and the film thicknesses of the first and second layer are unknown, in the same way as with the above-described implemented example. In this case, description can be made with reference to the flowchart shown in FIG. 4 described above, without change. In the present implemented example, analysis is made for a structure wherein a first layer of $SiO_2$ and a second layer of $SiN_x$ are formed on a substrate (Sub) of Si.

First, measurement is made for a sample having the aforementioned structure using an apparatus shown in FIG. 3. That is to say, the incident light is cast onto the thin-film double-layer structure on the substrate serving as a sample 4, which is to be measured, in order to obtain the change in polarization between the incident light and the reflected light while changing the wavelength of the incident light as a parameter. As a result, the $\psi_E$ and $\Delta_E$ spectrums, i.e., the $\psi_E(\lambda_i)$ and $\Delta_E(\lambda_i)$, which represent the change in polarization between the incident light and the reflected light, are obtained for each wavelength $\lambda_i$. Subsequently, the obtained data is stored as the comparative data.

In the analyzing stage 1B shown in FIG. 5, several models are formed based upon the plausible complex refractive indexes ($N_1$, ($n_1$, $k_1$)) and ($N_2$, ($n_2$, $k_2$)) of the materials ($SiO_2$, $SiN_x$) forming the films, and the plausible film thicknesses ($d_1$, $d_2$). In the present implemented example, let us say that four models (1) through (4) are formed as follows.

(Analyzing Step 1B-1)

The model (1) represents a film structure wherein a first layer (formed of a material having the optical constant of $SiO_2$, with the film thickness of $d_{11}$) and a second layer (formed of a material having the optical constants of $Si_3N_4$, with the film thickness of $d_{21}$) are formed on a substrate (Sub:Si).

The model (2) represents a film structure wherein a first layer (formed of a material having the optical constants of $SiO_2$, with the film thickness of $d_{12}$) and a second layer (formed of a material having the optical constant of $Si_3N_4$, and Void, with predetermined volume fraction and the film thickness of $d_{22}$) are formed on a substrate (Sub:Si). Note that the aforementioned Void represents a material having the refractivity of cavities, which is 1.

The model (3) represents a film structure wherein a first layer (formed of a material having the optical constants of $SiO_2$, with the film thickness of $d_{13}$) and a second layer (formed of a material having the optical constant of $Si_3N_4$ and a material having the optical constants of $SiN_x$, with the film thickness of $d_{23}$) are formed on a substrate (Sub:Si). Note that the aforementioned second layer 2 is formed of a mixture of the $Si_3N_4$ and $SiN_x$ with a predetermined volume fraction.

The model (4) represents a film structure wherein a first layer (formed of a material having the optical constants of $SiO_2$, with the film thickness of $d_{14}$) and a second layer (formed of a material having the optical constants of $SiN_x$ (known optical constants of a sample with a similar composition are used) and the Void, with the film thickness of $d_{24}$) are formed on a substrate (Sub:Si). Here, the second layers in the aforementioned models (2) through (4) can be approximated as a uniform film using the Effective Medium Approximation (EMA), thereby obtaining optical constants of the approximated uniform film based upon the volume fractions set to the second layer thereof.

Note that the above-described four models are formed, making an assumption that the optical constants of the material forming the substrate (Sub) are known, the optical constants of $SiO_2$ forming the first layer are generally known, and the optical constants of $SiN_x$ forming the second layer, the film thickness $d_1$ of the first layer, and the film thickness $d_2$ of the second layer, are unknown (uncertain).

(Analyzing Step 1B-2)

Fitting is performed with regard to each of the four models (1) through (4) formed in the above-described step 1B-1, and the measured data $\psi_E$ and $\Delta_E$ obtained from the above-described measured spectrums. The mean square error values ($\chi^2$) obtained at the time of fitting for the fitting parameters of each model are shown in block 32 in FIG. 5.

During the fitting of the model (1), fitting is performed for the film thickness of $d_{11}$ of the first layer and the film thickness of $d_{21}$ of the second layer, whereby the fitting results $d_{11(best)}$ and $d_{21(best)}$, and the mean square value $\chi^2_{(1)}$, are obtained.

During the fitting of the model (2), fitting is performed for the film thickness of $d_{12}$ of the first layer, the film thickness of $d_{22}$ of the second layer, and the volume fraction of the second layer, whereby the fitting results $d_{12(best)}$, $d_{22(best)}$, $Vf_{22(best)}$, and the mean square value $\chi^2_{(2)}$, are obtained.

During the fitting of the model (3), fitting is performed for the film thickness of $d_{13}$ of the first layer, the film thickness of $d_{23}$ of the second layer, and the volume fraction of the second layer, whereby the fitting results $d_{13(best)}$, $d_{23(best)}$, $Vf_{23(best)}$, and the mean square value $\chi^2_{(3)}$, are obtained.

During the fitting of the model (4), fitting is performed for the film thickness of $d_{14}$ of the first layer, the film thickness of $d_{24}$ of the second layer, and the volume fraction of the second layer, whereby the fitting results $d_{14(best)}$, $d_{24(best)}$, $Vf_{24(best)}$, and the mean square value $\chi^2_{(4)}$, are obtained.

(Analyzing Step 1B-3)

In this step shown in block 33 in FIG. 5, the fitting results corresponding to the model which exhibits the minimal $\chi^2$ value, or the fitting results, of which the film thicknesses and the volume fraction are in predetermined ranges, corresponding to the model which exhibits the minimal $\chi^2$ value, are selected from the fitting results obtained in the fitting for the aforementioned multiple models.

Note that the processing from analyzing step 2B-1 to analyzing step 3B-3 is performed in the same way as described above.

(Description Regarding an Implemented Example of an Analysis Method for Analyzing a Thin-film Multi-layer Structure)

Description will be made below regarding an analysis method for analyzing a thin-film multi-layer structure based upon spectroscopic data acquired from a spectroscopic ellipsometer according to the present invention with reference to the drawings and the like.

Figure 8:
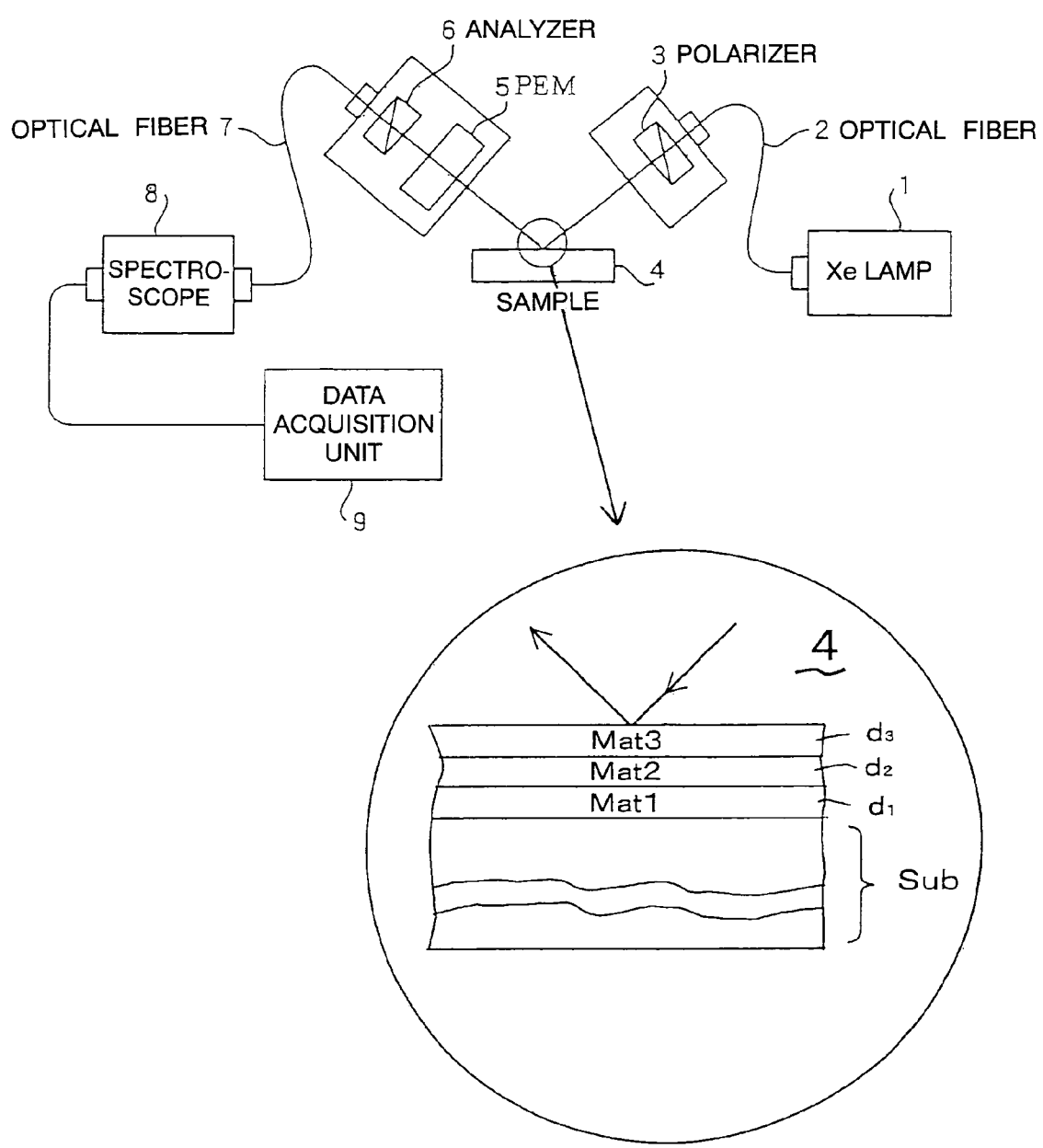
FIG. 8 is a schematic diagram which shows a configuration of an ellipsometer employed in an extremely-thin-film multi-layer-structure measurement method according to an embodiment of the present invention, wherein a part of the sample which is to be measured is enlarged.

FIG. 8 is a schematic diagram which shows a configuration of an ellipsometer employed in the analysis method for analyzing a thin-film multi-layer structure.

In general, the present invention can be applied to an analysis method for analyzing an extremely-thin-film multi-layer structure and a thin-film multi-layer structure, having two or more layers. First, description will be made regarding an extremely-thin-film triple-layer structure as an example, for simplification. Note that FIG. 8 shows an enlarged part of the sample 4 which is to be measured.

The processing shown in the step for acquiring the spectroscopic measurement data described later is performed using the spectroscopic ellipsometer shown in FIG. 8. First, description will be made regarding the measurement apparatus. A Xe lamp 1 is a so-called white light source for emitting light containing a great number of wavelength components. The light emitted from the Xe lamp 1 is introduced to a polarizer 3 through an optical fiber 2. The light polarized by the polarizer 3 is cast onto the surface of a sample 4 which is to be measured with a predetermined incident angle (e.g., $\phi=75°$). Note that the sample 4 is a measurement sample wherein three thin-film layers are formed on a substrate described later.

The reflected light from the sample 4 is introduced to an analyzer 6 through a photo-elastic modulator (PEM) 5. The reflected light is subjected to phase modulation with a frequency of 50 kHz by the photo-elastic modulator (PEM) 5. As a result the polarization of the reflected light, which is originated from the linearly polarized incident light, will change periodically from linearly to elliptically. Accordingly, $\Psi$ and $\Delta$ can be determined within several msec. The output from the analyzer 6 is connected to a spectroscope 8 through an optical fiber 7. The output data from the spectroscope 8 is acquired by a data acquisition unit 9, whereby the spectroscopic measurement step to obtain the measured spectroscopic data ends. Note that the PEM 5 may be situated in front of the polarizer 3 or the analyzer 6.

Figure 9:
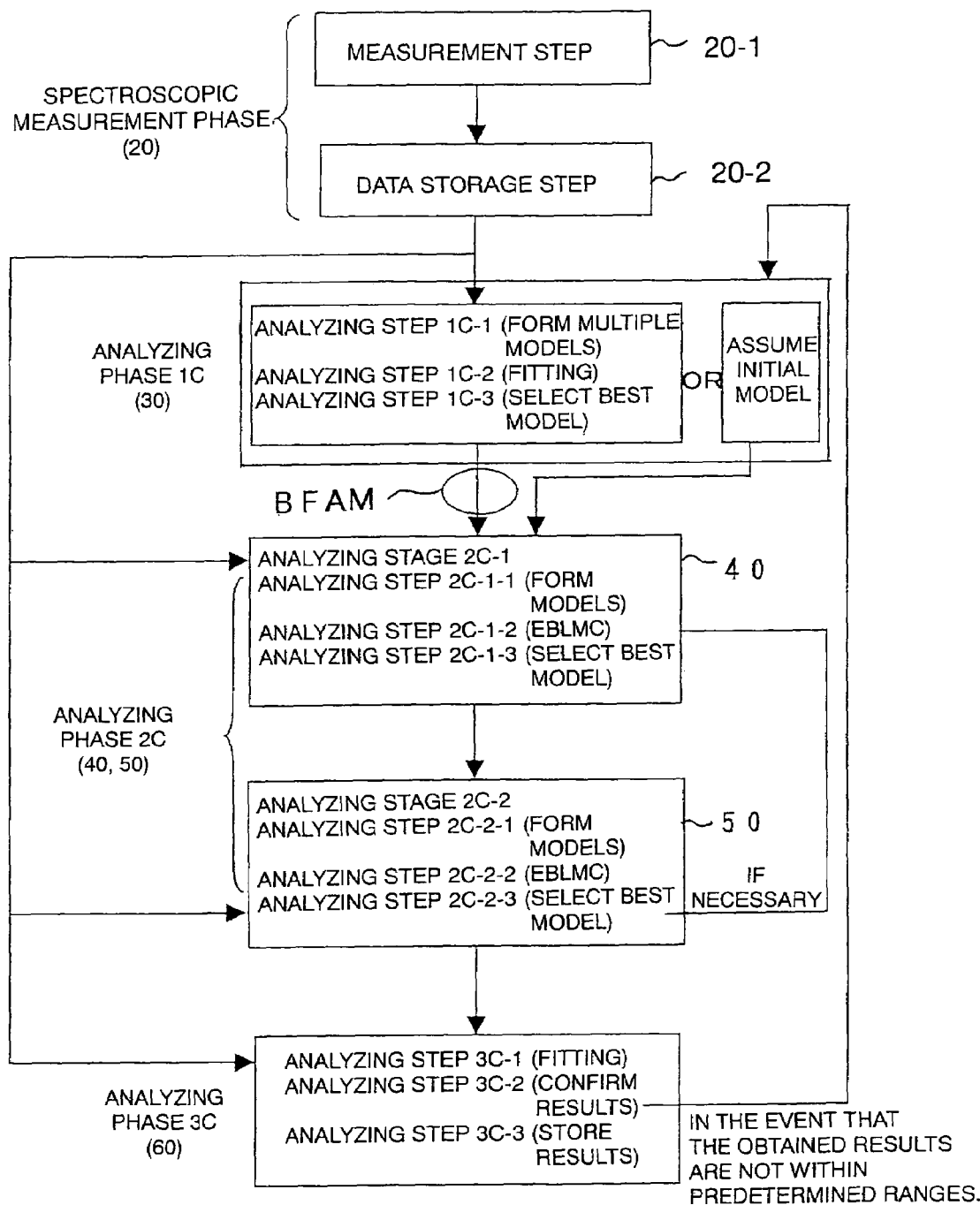
FIG. 9 is a flowchart which shows an extremely-thin-film triple-layer-structure measurement method according to an embodiment of the present invention.
Figure 15:
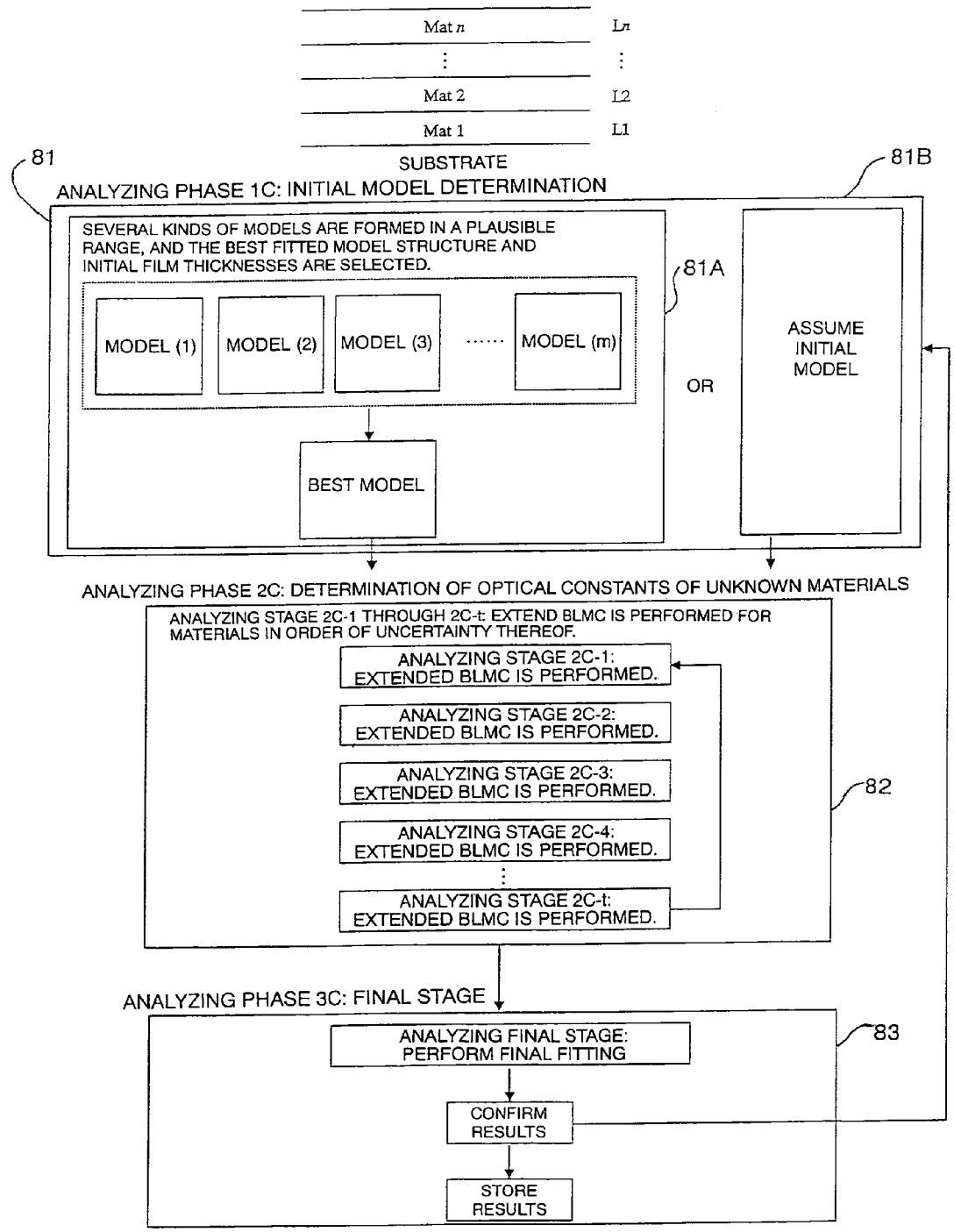
FIG. 15 is a flowchart for describing a thin-film n-layer-structure measurement method, which is a generalized arrangement according to the present invention.

FIG. 9 is a flowchart which shows an extremely-thin-film triple-layer measurement method, and FIG. 15 is a flowchart which shows an analysis method for analyzing a thin-film n-layer structure, which is a generalized arrangement according to the present invention.

Generally, the analysis method according to the present invention can be classified into three phases for facilitating discussion. In analyzing phase 1C, the initial model, which is to be analyzed in steps following analyzing phase 2C, and is assumed to match an actual sample, is determined.

In the phase 1C, as described later, an arrangement may be made wherein a single best-first-approximation model (which will be referred to as "BFAM" hereafter) is selected as the initial model from multiple models by fitting (see the blocks 31, 32, and 33, in FIG. 10, and the block 81A in FIG. 15), or an arrangement may be made wherein the initial model is assumed or formed based upon known data (see the block 34 in FIG. 10, and the block 81B in FIG. 15). In either case, the selected initial model in the phase 1 is analyzed in steps from the analyzing phase 2C on.

The number of models, from which the aforementioned model (BFAM) are selected in analyzing phase 1C, is dependent upon the number of unknown layers in a structure of a sample and the number of available data sets. Note that the unknown layer used here means a layer or the like of which the precise optical constants need to be determined.

In the analyzing phase 2C, the EBLMC method is performed for unknown materials forming multi-layer structure. Specifically, the EBLMC method is performed for each unknown material in order of uncertainty thereof in the analyzing stage 2C-1, the analyzing stage 2C-2, and so forth.

For example, in the analyzing stage 2C-1, the EBLMC method is performed for the Mat 2 as described later. Subsequently, in analyzing stage 2C-2, the EBLMC method is performed for the Mat 3 using the results obtained in the analyzing stage 2C-1. In the analyzing phase 3C, final fitting is made for the results obtained in the analyzing phase 2C, and the obtained data is confirmed, and output or stored.

Now, reference characters are listed as follows.

(Definition of the Reference Characters)

Sub: substrate (with known optical constants, which serves as a bulk)

Mat: material forming a thin film (optical constants of the material)

$d_i$: film thickness of the i'th layer $d_{i(best)}$: film thickness of the i'th layer obtained by fitting $d_{ij}$: film thickness of the i'th layer in the j'th model $d_{ij(best)}$: film thickness of the i'th layer in the j'th model obtained by fitting $\chi^2$: mean square error ($\chi^2$)

$\chi^2_{(j)}$: mean square error ($\chi^2$) at the time of fitting based upon the j'th model Void: material with n=1, and k=0

$Vf_{(ij)}$: volume fraction of the material in the i'th layer in the j'th model $Vf_{(ij)(best)}$: volume fraction of the material in the i'th layer in the j'th model obtained by fitting Now, description will be made regarding an implemented example for analyzing a sample having a structure as follows.

| | | |
|---|---|---|
| The third layer: | $TaO_x$ ($Mat_3$): | $d_3$ |
| The second layer: | SiN ($Mat_2$): | $d_2$ |
| The first layer: | $SiO_2$ ($Mat_1$): | $d_1$ |
| Substrate (Sub): | Si: | bulk |

Measurement shown in block 20-1 (measurement step in the spectroscopic measurement phase) in FIG. 9 is performed using an apparatus shown in FIG. 8. The incident light is cast onto an extremely-thin-film triple-layer structure on the substrate (see the enlarged view in the drawing) serving as a sample 4 in order to obtain the change in polarization between the incident light and the reflected light while changing the wavelength of the incident light as a parameter. As a result, the $\psi_E$ and $\Delta_E$ spectrums, i.e., the $\psi_E(\lambda_i)$ and $\Delta_E(\lambda_i)$, which represent the change in polarization between the incident light and the reflected light, are obtained for each wavelength $\lambda_i$. In the data storage block 20-2 in the spectroscopic measurement phase, the data obtained in the previous step is stored as the comparative data (see FIG. 9).

(Extremely-thin-film Triple-layer-structure Fitting Process)

Next, description will be made regarding an implemented example for analyzing a structure wherein the optical constants of the material 1 (Mat 1) forming the first layer are generally known, and the optical constants of the materials 2 and 3 forming the second and third layers and the film thicknesses ($d_1$, $d_2$, and $d_3$) of the first, second, and third layers are unknown. Note that, in this example, let us say that the optical constants of the second layer are the least known.

Figure 10:
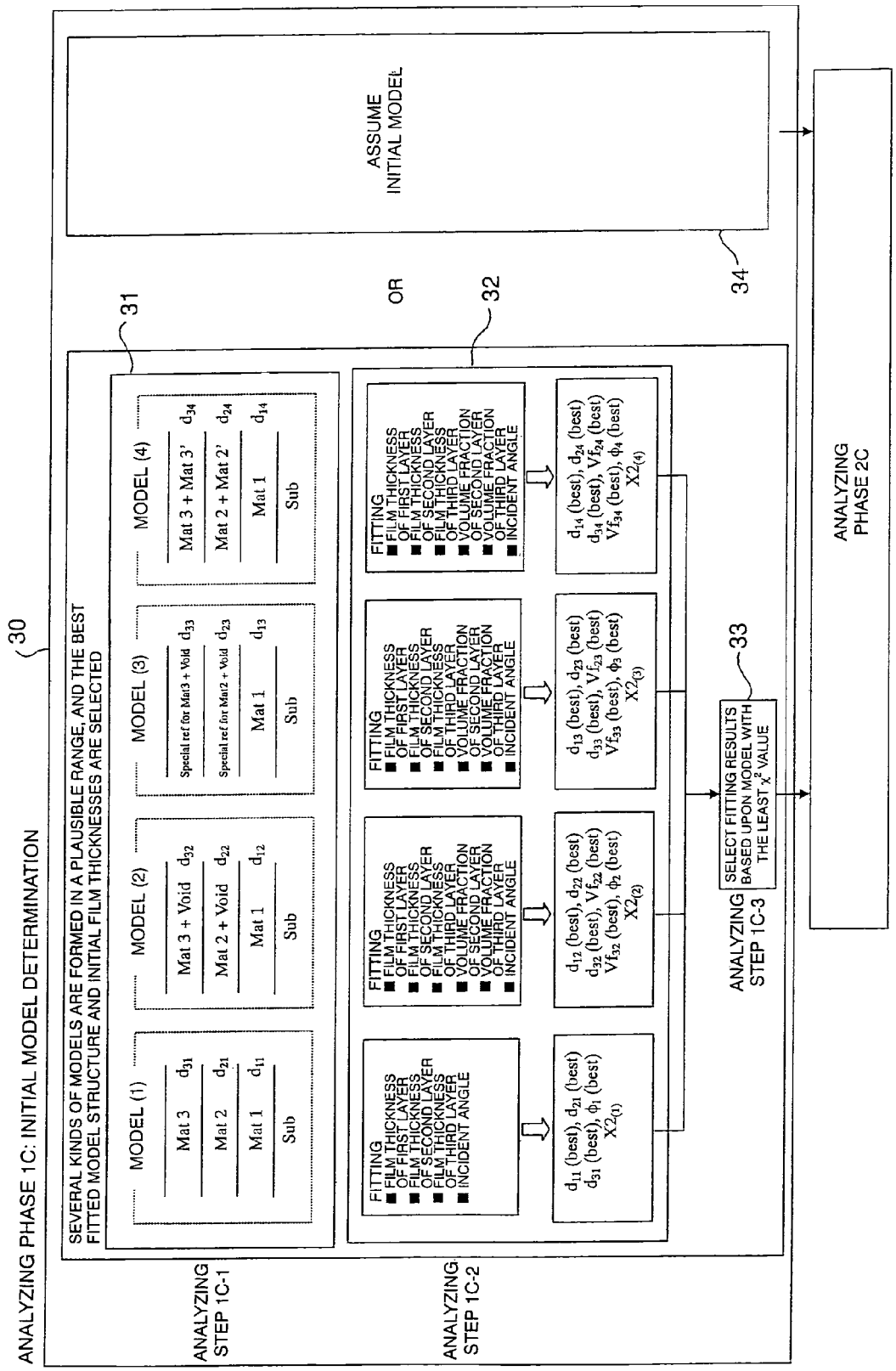
FIG. 10 is an explanatory diagram for describing an analyzing phase 1C of the aforementioned embodiment in detail.

In the analyzing phase 1C, the processing described in blocks 31 through 33 shown in FIG. 10 are performed, whereby the BFAM is determined as an initial model. Alternately, the initial model is assumed as shown in block 34 in FIG. 10.

(Analyzing Step 1C-1)

As shown in block 31 in FIG. 10, multiple kinds of plausible models are formed. Subsequently, the model having the structure and the film thicknesses which match the measured results best in the initial stage is determined.

In this step, several models are formed based upon the ($N_0$, ($n_0$, $k_0$)) of the substrate, and the plausible complex refractive indexes ($N_1$, ($n_1$, $k_1$)), ($N_2$, ($n_2$, $k_2$)), and ($N_3$, ($n_3$, $k_3$)) of the materials (Mat 1, Mat 2, Mat 3) forming the thin films, and the film thicknesses ($d_1$, $d_2$, $d_3$).

In the present implemented example, let us say that four models (1) through (4) are formed as follows. Note that the schematic structures of the aforementioned models are shown in block 31 in FIG. 10.

The model (1) represents a film structure wherein a first layer (formed of a material having the optical constants of the Mat 1, with the film thickness of $d_{11}$), a second layer (formed of a material having the optical constants of the Mat 2 with the film thickness of $d_{21}$), and a third layer (formed of a material having the optical constants of the Mat 3 with the film thickness of $d_{31}$), are formed on a substrate (Sub).

The model (2) represents a film structure wherein a first layer (formed of a material having the optical constants of the Mat 1, with the film thickness of $d_{12}$), a second layer (formed of a material having the optical constants of the Mat 2, and the Void, with the film thickness of $d_{22}$), and a third layer (formed of a material having the optical constants of the Mat 3, and the Void, with the film thickness of $d_{32}$), are formed on a substrate (Sub). Note that the aforementioned Void represents a material having the refractivity of cavities, which is 1.

The model (3) represents a film structure wherein a first layer (formed of a material having the optical constants of the Mat 1, with the film thickness of $d_{13}$), a second layer (formed of a material having the optical constants obtained by measuring a material similar to the Mat 2, and the Void, with the film thickness of $d_{23}$), and a third layer (formed of a material having the optical constants obtained by measuring a material similar to the Mat 3, and the Void, with the film thickness of $d_{33}$), are formed on a substrate (Sub).

The model (4) represents a film structure wherein a first layer (formed of a material having the optical constants of the Mat 1, with the film thickness of $d_{14}$), a second layer (formed of a material having the optical constants of the Mat 2, and a material having the optical constants of the Mat 2', with the film thickness of $d_{24}$), and a third layer (formed of a material having the optical constants of the Mat 3, and a material having the optical constants of the Mat 3', with the film thickness of $d_{34}$), are formed on a substrate (Sub).

Here, each of the second layer and the third layer in the aforementioned models (2) through (4) can be approximated as uniform films using the Effective Medium Approximation (EMA), thereby obtaining optical constants of the approximated uniform films based upon the volume fraction set to the second layer and the third layer thereof. Note that the above-described four models are formed, making an assumption that the optical constants of the material forming the substrate (Sub) are known, the optical constants of the first layer are generally known, and the optical constants of the second layer and the third layer, the film thickness $d_1$ of the first layer, the film thickness $d_2$ of the second layer, and the film thickness $d_3$ of the third layer, are unknown (uncertain).

(Analyzing Step 1C-2)

Fitting is performed with regard to each of the four models (1) through (4) formed in the above-described analyzing step 1C-1, and the measured data $\psi_E$ and $\Delta_E$ obtained from the above-described measured spectrums. The mean square error values ($\chi^2$) obtained at the time of fitting for the fitting parameters of each model are shown in block 32 in FIG. 10.

During the fitting of the model (1), fitting is performed for the film thickness of $d_{11}$ of the first layer, the film thickness of $d_{21}$ of the second layer, the film thickness of $d_{31}$ of the third layer, and the incident angle $\phi_1$, whereby the fitting results $d_{11(best)}$, $d_{21(best)}$, $d_{31(best)}$, $\phi_{1(best)}$, and the mean square value ($\chi^2$ value) $\chi^2_{(1)}$, are obtained.

During the fitting of the model (2), fitting is performed for the film thickness of $d_{12}$ of the first layer, the film thickness of $d_{22}$ of the second layer, the film thickness of $d_{32}$ of the third layer, the volume fraction $Vf_{22}$ of the second layer, the volume fraction $Vf_{32}$ of the third layer, and the incident angle $\phi_2$, whereby the fitting results $d_{12(best)}$, $d_{22(best)}$, $d_{32(best)}$, $Vf_{22(best)}$, $Vf_{32(best)}$, $\phi_{2(best)}$, and the mean square value ($\chi^2$ value) $\chi^2_{(2)}$, are obtained.

During the fitting of the model (3), fitting is performed for the film thickness of $d_{13}$ of the first layer, the film thickness of $d_{23}$ of the second layer, the film thickness of $d_{33}$ of the third layer, the volume fraction $Vf_{23}$ of the second layer, the volume fraction $Vf_{33}$ of the third layer, and the incident $\phi_3$, whereby the fitting results $d_{13(best)}$, $d_{23(best)}$, $d_{33(best)}$, $Vf_{23(best)}$, $Vf_{33(best)}$, $\phi_{3(best)}$, and the mean square value ($\chi^2$ value) $\phi^2_{(3)}$, are obtained.

During the fitting of the model (4), fitting is performed for the film thickness of $d_{14}$ of the first layer, the film thickness of $d_{24}$ of the second layer, the film thickness of $d_{34}$ of the third layer, the volume fraction $Vf_{24}$ of the second layer, the volume fraction $Vf_{34}$ of the third layer, and the incident angle $\phi_4$, whereby the fitting results $d_{14(best)}$, $d_{24(best)}$, $d_{34(best)}$, $Vf_{24(best)}$, $Vf_{34(best)}$, $\phi_{4(best)}$, and the mean square value ($\chi^2$ value) $\chi^2_{(4)}$, are obtained.

(Analyzing Step 1C-3)

In this step, the fitting results corresponding to the model which exhibits the minimal $\chi^2$ value, or the fitting results, of which the film thicknesses, the volume fractions, and the incident angle, are in predetermined ranges, corresponding to the model which exhibits the minimal $\chi^2$ value, are selected from the fitting results obtained in the fitting for the aforementioned multiple models, as shown in block 33 in FIG. 10.

In the analyzing phase 2C, EBLMC is performed in order of uncertainty of the material.

Figure 11:
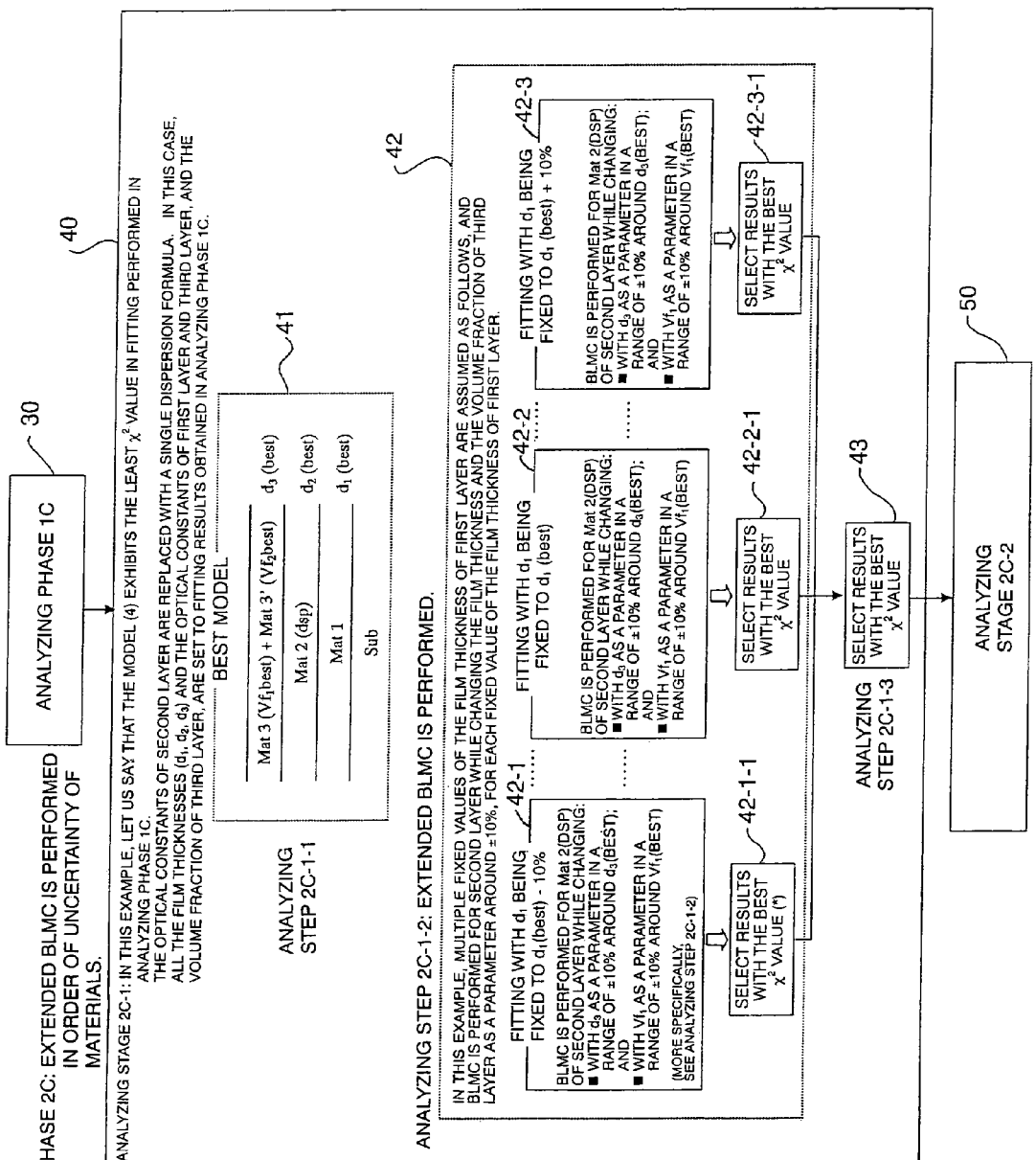
FIG. 11 is an explanatory diagram for describing an analyzing phase 2B stage 1 (stage 2B-1) of the aforementioned embodiment in detail.

The BFAM, which serves as a model employed in the analyzing phase 2C, is shown in block 41 in FIG. 11.

In this example, let us say that the fitting results based upon the model (4) in the analyzing phase 1C exhibits the minimal $\chi^2$ value. Here, the optical constants of the second layer are replaced by a single dispersion formula. In this case, all the film thicknesses ($d_1$, $d_2$, $d_3$), the optical constants of the first and third layers, and the volume fraction of the third layer, are determined based upon the fitting results obtained in the above-described analyzing phase 1C.

(Analyzing Step 2C-1-2)

Figure 14:
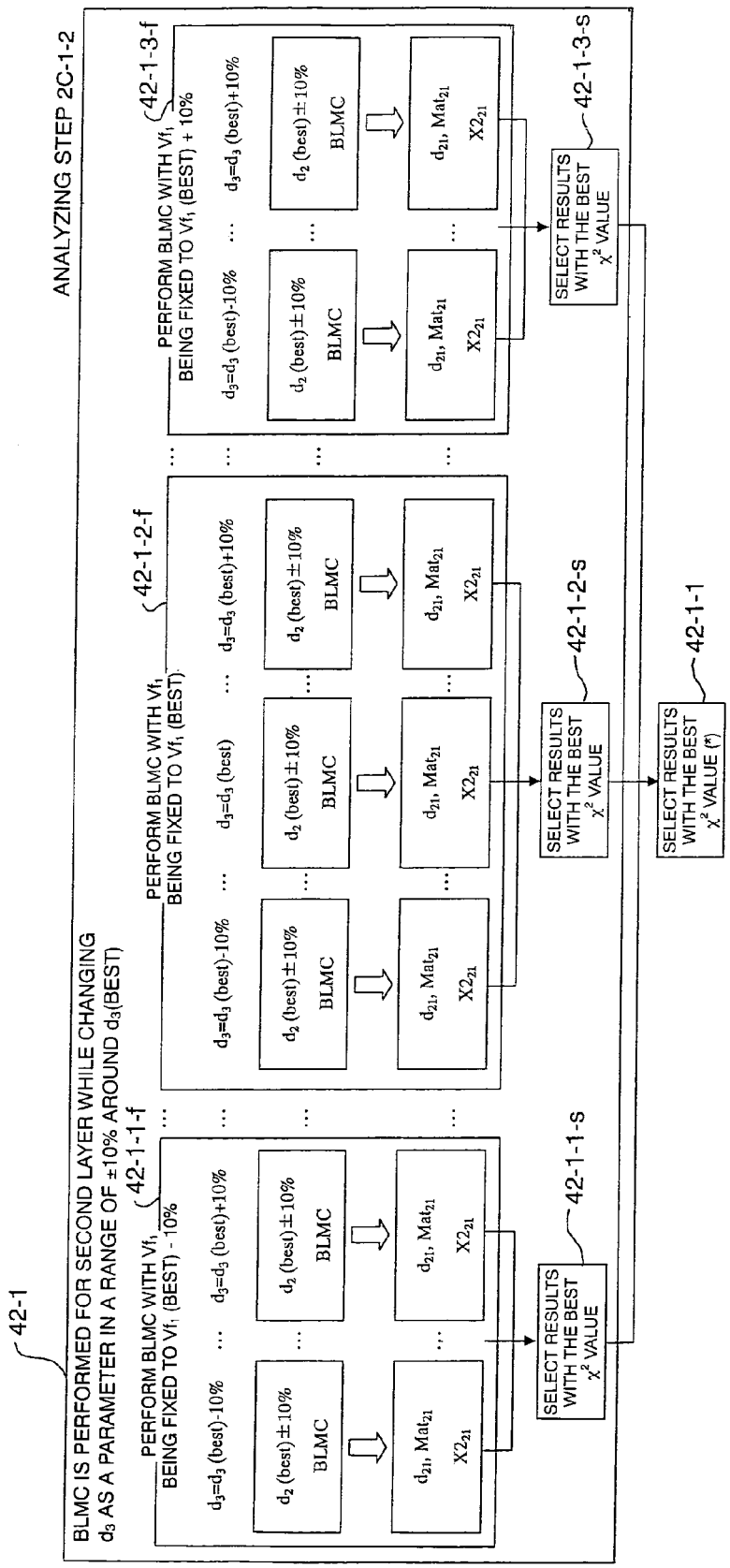
FIG. 14 is an explanatory diagram for describing a part of an analyzing phase 2B stage 1 step 2 (step 2B-1-2) of the aforementioned embodiment in detail.

In this example, as shown in FIG. 11, BLMC is performed for the second layer with the film thickness of the first layer fixed to the value described below, while changing both the film thickness of the third layer and the volume fraction thereof around ±10% as parameters. In a step shown in block 42-1, BLMC is performed for the Mat 2 (DSP) of the second layer with the film thickness $d_1$ of the first layer fixed to the $d_{1(best)}$−10%, while changing the film thickness $d_3$ within around $d_{3(best)}$±10%, and the volume fraction $Vf_1$ within around $Vf_{1(best)}$±10%. The above-described step shown in block 42-1 (in a case wherein $d_1$ is fixed to the $d_{1(best)}$−10%) is shown in detail in FIG. 14.

First, description will be made regarding a step shown in block 42-1-2-*f* as an example. In this case, BLMC is performed for the second layer with the $Vf_1$ fixed to $Vf_{1(best)}$ while changing the film thickness $d_3$ within ±10% around $d_{3(best)}$, whereby fitting results, i.e., the film thicknesses, the optical constants thereof, and the $\chi^2$ value, are obtained for each film thickness $d_3$ as a parameter. The fitting results which exhibits the minimal $\chi^2$ value is selected as the fitting results in the step shown in block 42-1-2-*s*. The same processing as in block 42-1-2-*f* is performed in the steps shown in blocks 42-1-1-*f*, 42-1-3-*f*, and so forth, with the $Vf_1$ being fixed to a predetermined value within ±10% around $Vf_{1(best)}$. In each case, the best fitting results which exhibit the minimal $\chi^2$ value are selected in blocks 42-1-1-*s*, 42-1-3-*s*, and so forth, as well. Furthermore, the best fitting results which exhibit the minimal $\chi^2$ value are selected from the aforementioned fitting results obtained based upon the models with the $Vf_1$ as a parameter (see FIG. 11 and block 42-1-1 in FIG. 14).

Furthermore, in step shown in block 42-2 in FIG. 11, BLMC is performed with the $d_1$ fixed to the $d_{1(best)}$, in the same way as shown in block 42-1 described above. Furthermore, in step shown in block 42-3 in FIG. 11, BLMC is performed with the $d_1$ fixed to the $d_{1(best)}$±10%, in the same way as shown in block 42-1 described above. In each case, the best fitting results which exhibit the minimal $\chi^2$ value are selected in blocks 42-2-1, 42-3-1, and so forth, in the same way as in the aforementioned block 42-1-1. Furthermore, the best fitting results which exhibit the minimal $\chi^2$ value are selected from the aforementioned fitting results obtained based upon the models with the $d_1$ as a parameter (see block 43 in FIG. 11).

(Analyzing Phase 2C-2-1)

Figure 12:
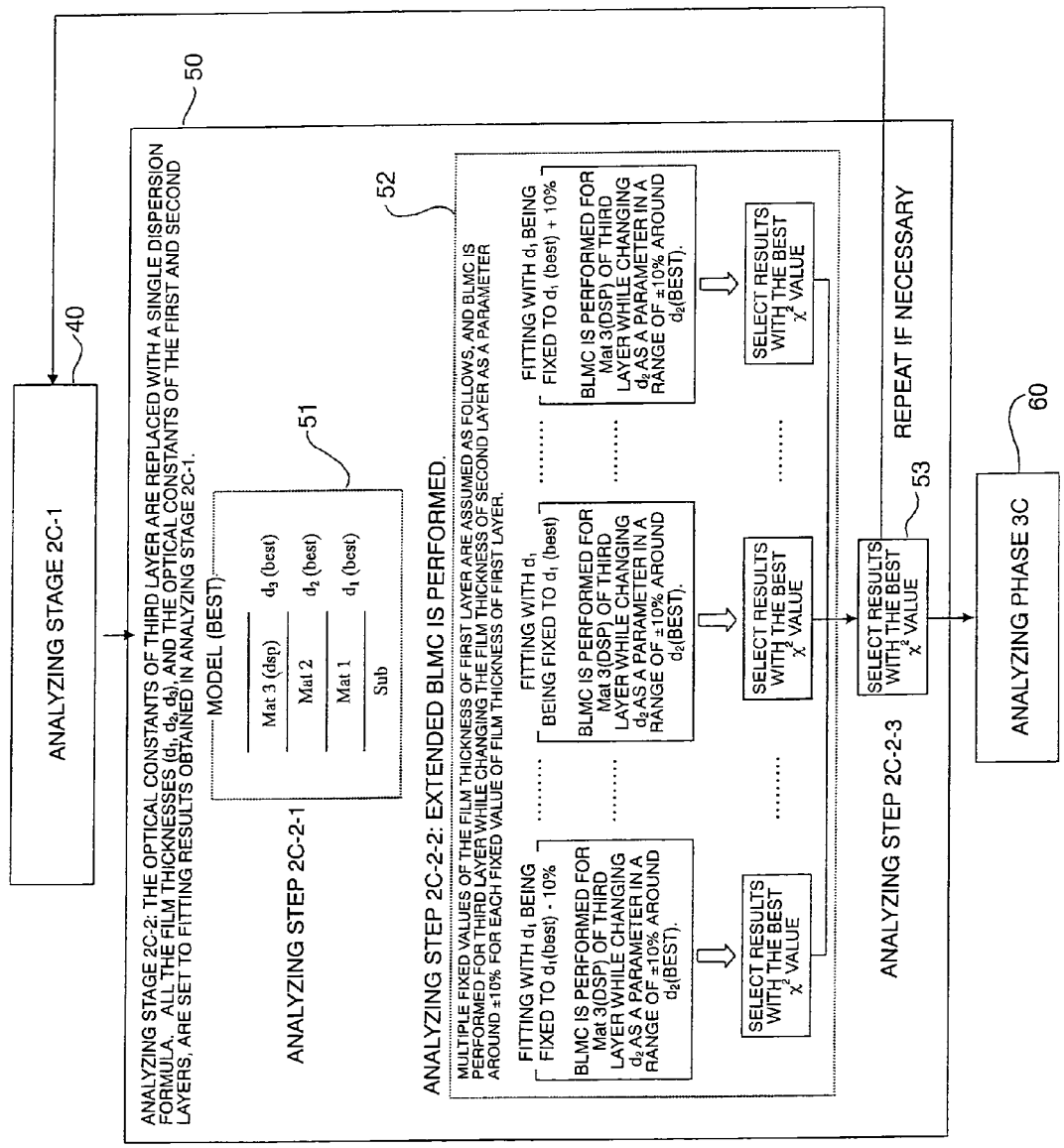
FIG. 12 is an explanatory diagram for describing an analyzing phase 2B stage 2 (stage 2B-2) of the aforementioned embodiment in detail.

In the analyzing phase 2C-2-1, the optical constants of the third layer are replaced by a single dispersion formula as shown in FIG. 12 (see step 1 shown in block 51 in FIG. 12). All the film thicknesses ($d_1$, $d_2$, $d_3$), and the optical constants of the first and second layers, are determined based upon the fitting results in the analyzing stage 2C-1.

(Analyzing Step 2C-2-2)

EBLMC is performed for the model determined in the aforementioned step 2C-2-1. Specifically, BLMC is performed for the third layer while changing the film thickness $d_1$ of the first layer as a parameter in a range of ±10% around $d_{1(best)}$, as well as changing the film thickness $d_2$ of the second layer as a parameter in the range of ±10% around $d_{2(best)}$.

(Analyzing Step 2C-2-3)

In the step shown in block 53 in FIG. 12, the best fitting results which exhibit the minimal $\chi^2$ value are selected from the aforementioned fitting results obtained in the above-described analyzing step 2C-2-2. Note that in the event that determined kinds of the fitting results, i.e., film thicknesses, the parameters of the dispersion formula, the volume fractions, and the incident angle, deviate from predetermined ranges, the flow returns to the analyzing stage 2C-1. Note that in the event that determined kinds of the fitting results are within the predetermined ranges, the flow proceeds next processing.

(Analyzing Step 3C-1)

Figure 13:
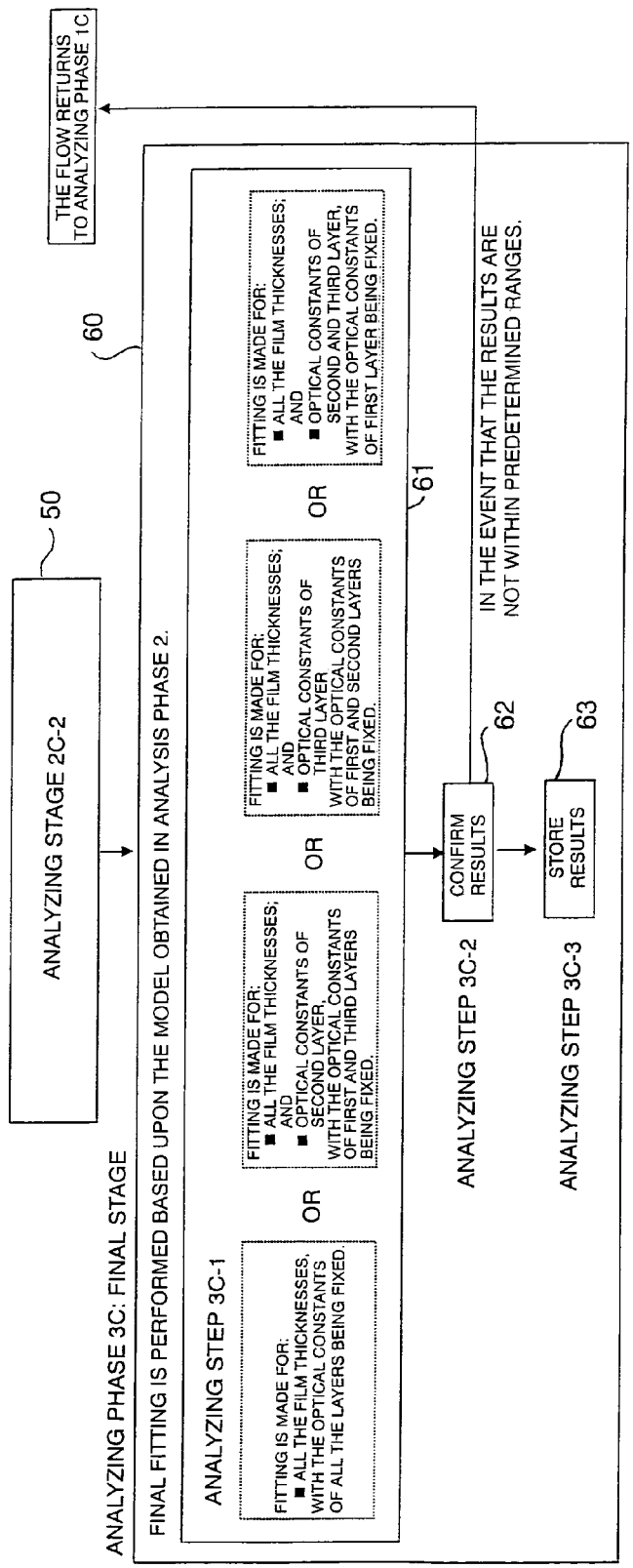
FIG. 13 is an explanatory diagram for describing an analyzing phase 3B of the aforementioned embodiment in detail.

FIG. 13 shows analyzing phase 3C serving as the final analyzing phase. In analyzing step 3C-1 shown in FIG. 13, fitting is made for the model, which exhibits the best $\chi^2$ value in the above-described analyzing step 2C-2-3, as follows.

Fitting is made for all the film thicknesses with all the optical constants thereof being fixed. Alternately, fitting is made for all the film thicknesses and the optical constants of the second layer with the optical constants of the first and third layers being fixed. Alternately, fitting is made for all the film thicknesses and the optical constants of the third layer with the optical constants of the first and second layers being fixed. Alternately, fitting is made for all the film thicknesses and the optical constants of the second and third layers with the optical constants of the first layer being fixed.

(Analyzing Step 3C-2)

In analyzing step 3C-2 shown in block 62 in FIG. 13, confirmation is made for fitting results obtained in the above-described analyzing step 3C-1. For example, confirmation is made whether or not the obtained fitting results are within predetermined ranges. In the event that determination is made that the obtained fitting results deviate from the predetermined ranges, the flow returns to the above-described analyzing phase 1C.

(Analyzing Step 3C-3)

In analyzing step 3C-3 shown in block 63 in FIG. 13, the fitting results which have passed the aforementioned confirmation described in analyzing step 3C-2 are stored.

According to the present invention:

1. Reliable film thicknesses (of all the layers) and optical constants (of at least two layers in a film structure) can be obtained, even for a multi-layer structure (in particular, Ultra-thin-film multi-layer structure) in spite of the strong correlation there between.

2. In BFAM determination step, the number of required plausible unknown variables can be suppressed to a minimum.

3. EBLMC is performed in an appropriate order, thereby drastically reducing the possibility to obtain wrong local minimum, and thereby improving the reliability of the fitting results.

4. With the method according to the present invention, the film thicknesses and the optical constants of a multi-layer structure can be determined, even in a case wherein the multi-layer structure contains a large number of unknown materials.

Various modifications can be made within the scope of the present invention. To facilitate understanding, description has been made regarding acquisition of data and setting of models, using $\Psi$ and $\Delta$, throughout the present specification. Furthermore, the measurement and fitting can be performed in the same way for data set of (n, k), ($\epsilon_i$, $\epsilon_r$), (tan $\Psi$, cos $\Delta$), or ($I_s$, $I_c$), well known by one skilled in the art, and are encompassed in the present invention.

While description has been made regarding an implemented example for analyzing a single-layer structure wherein a $SiO_x$ or SiON layer are formed on a substrate, an implemented example for analyzing a double-layer structure wherein $SiO_2$ and $SiN_x$ layers are formed on a substrate, or an implemented example for analyzing a triple-layer structure wherein $SiO_2$, $SiN_x$, and $TaO_x$ layers are formed on a substrate, the present invention may be applied to a single-layer structure or multi-layer structure formed of a wide variety of materials in a wide range of film thickness in the same way.

While description has been made regarding an arrangement wherein known values (reference data) are employed for the optical constants, an arrangement may be made wherein the optical constants are calculated based upon the dispersion formula or the like which represents the wavelength dependency of the dielectric constant of the material, which is encompassed in the technical scope of the present invention. Furthermore, in a case of using a dispersion formula, an arrangement may be made wherein known values are employed for optical constants, which is encompassed in the technical scope of the present invention.

While description has been made regarding an arrangement wherein measurement is made using an ellipsometer with the PEM, an arrangement may be made wherein measurement is made using an ellipsometer without the PEM.

The present invention can be similarly applied to an arrangement wherein a substrate other than Si substrate, such as a transparent substrate formed of glass, quartz, or the like, a compound semiconductor substrate, or the like, is employed. Furthermore, the present invention is not restricted to any particular kind of substrate, but rather the present invention can be applied to a substrate with any surface state, i.e., the present invention can be applied to both smooth and rough substrates.

The dispersion formulas used for the present invention include not only the formula based upon classical mechanics or quantum mechanics and empirical formulas, but also various other formulas including other parameters, which are encompassed in the technical scope of the present invention.

While description has been made regarding an arrangement wherein measurement is made using the EMA, an arrangement may be made wherein other effective medium theory is employed, which is also encompassed in the technical scope of the present invention.

Part or all of the above described methods can be performed automatically (by a computer, robot, or the like) or manually, which is also encompassed in the technical scope of the present invention.

Description has been made regarding an arrangement wherein measurement is made with an incident angle of 75°, but an arrangement may be made wherein measurement is made with an incident angle other than the aforementioned angle, which is also included in the technical scope of the present invention.

While description has been made regarding a method for analyzing by taking an incident angle around the nominal incident angle (75°) as a parameter, an arrangement may be made wherein analysis is made taking an incident angle around the measured incident angle as a parameter, which is also encompassed in the technical scope of the present invention.

Furthermore, an arrangement may be made wherein measurement is made with multiple incident angles automatically (Variable Angle Measurement), and analysis is made based upon all of the measured data, or based upon the data with regard to a specified angle of the aforementioned multiple incident angles, which is also encompassed in the technical scope of the present invention. Furthermore, an arrangement may be made wherein fitting is performed for all of the measured data, or for the data with regard to the specified incident angle, taking an incident angle around each measuring incident angle as a parameter, which is encompassed in the technical scope of the present invention.

While description has been made regarding an implemented example for analyzing a single-layer structure, a double-layer structure, or a triple-layer structure, formed of extremely-thin-films (Mat 1, Mat 2, Mat 3) on a substrate, the present invention is not restricted to an arrangement for analyzing a structure formed of extremely-thin-film dielectric materials, rather, the present invention may be applied to an arrangement for analyzing a structure formed of a wide variety of materials in a wide range of film thickness in the same way.

Furthermore, an arrangement may be made wherein all or a part of the above-described method are performed, which is also encompassed in the technical scope of the present invention.

While description has been made regarding an implemented example for performing fitting with regard to desired parameters at the same time, an arrangement may be made wherein the parameters are divided into multiple groups so as to perform fitting for each parameter group, which is also encompassed in the technical scope of the present invention.

In some cases, fitting is made for the incident angle with BLMC forming a part of EBLMC, as described above. In this case, description has been made regarding an implemented example for performing fitting with regard to the incident angle and a wide variety of parameters at the same time, an arrangement may be made wherein separate fitting is made for the incident angle and the other parameters, or an arrangement may be made wherein fitting is made for the parameters of the film structure with the incident angle being fixed, which are also encompassed in the technical scope of the present invention.

Furthermore, an arrangement may be made wherein fitting is made for the incident angle using fitting methods other than BLMC, which is also encompassed in the technical scope of the present invention.

While description has been made regarding an implemented example for performing BLMC or EBLMC for multiple models with a predetermined parameter being fixed at and around the median thereof in a range of ±10% in increments of 5%, an arrangement may be made for performing BLMC or EBLMC for multiple models with a predetermined parameter being fixed at and around the median thereof in other ranges and in other increments. Furthermore, while description has been made regarding an implemented example wherein the range and the increments of the aforementioned parameter have been expressed in terms of percent (%), an arrangement may be made wherein the range and the increments of the aforementioned parameter are expressed in terms of the minimal value, the maximal value, and the number of increment steps, which is also encompassed in the technical scope of the present invention.

While description has been made regarding an implemented example wherein EBLMC is performed for materials in order of uncertainty thereof, which is an effective method, an arrangement may be made wherein EBLMC is performed in other orders, which is also encompassed in the technical scope of the present invention.

While description has been made regarding an implemented example wherein the obtained data is stored in a step forming the measurement and analyzing step, an arrangement may be made wherein the obtained data is stored even following completion of the analysis process (i.e., the obtained data can be used following completion of the analysis process), or an arrangement may be made wherein the obtained data is temporarily stored during the analysis process, which are also encompassed in the technical scope of the present invention.

While description has been made regarding an implemented example wherein one through four models are formed based upon a mixture of $SiO_2$, $SiN_x$, $Si_3N_4$, and Void, in the model-preparation step, an arrangement may be made wherein these models are formed based upon a mixture of a wide variety of materials, which is also encompassed in the technical scope of the present invention. Note that the kind and the number of the model varies corresponding to the conditions at the time of manufacturing process, unknown data, or the like.

While description has been made regarding an implemented example wherein fitting is made for a combination of the incident angle and the film thicknesses, in some case, an arrangement may be made wherein fitting is made for the incident angle and the parameters of the dispersion formula at the same time, which is also encompassed in the technical scope of the present invention.

While description has been made regarding an implemented example wherein fitting is made using the mean square error, an arrangement may be made wherein fitting is made using parameters other than the $\chi^2$ value, which is also encompassed in the technical scope of the present invention.

While description has been made regarding an implemented example for analyzing a layer formed of a mixture of two materials, an arrangement may be made for analyzing a layer formed of a mixture of three or more materials, which is also encompassed in the technical scope of the present invention.

What is claimed is:

1. An extremely-thin-film measurement and thin-film measurement method for analyzing spectroscopic data acquired from a spectroscopic ellipsometer using best-local-minimum-calculation (BLMC), said method comprising:
    a spectrum measurement step wherein incident light is cast onto a thin film on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light;
    a step for assuming the complex refractive index ($N_0$ ($n_0$, $k_0$)) of said substrate, the complex refractive index (N (n, k)) of said film, based upon the dispersion formula, a plurality of film thicknesses within a plausible range, and a plurality of incident angles within a plausible range;
    a step for performing fitting for the parameters of the dispersion formula (DSP) based upon combinations of said incident angle and said film thickness;
    a first analyzing step for selecting fitting results obtained based upon a model formed of a combination of said film thickness and said incident angle, which exhibits the minimal difference between the $\Psi_M(\lambda_i)$ and $\Delta_M(\lambda_i)$ obtained by said fitting and said measured $\Psi_E(\lambda_i)$ and $\Delta_E(\lambda_i)$; and
    a second analyzing step for performing fitting for the film thickness and the dispersion formula with the incident angle obtained in said first analyzing step being fixed.

2. An extremely-thin-film measurement and thin-film measurement method for analyzing spectroscopic data acquired from a spectroscopic ellipsometer using best-local-minimum-calculation (BLMC) according to claim 1, wherein in said first analyzing step and second analyzing step, the mean square error ($\chi^2$) is calculated from the measured values and the fitting results for each model, and the fitting results which exhibit the minimal mean square error ($\chi^2$) are selected.

3. An extremely-thin-film measurement and thin-film measurement method for analyzing spectroscopic data acquired from a spectroscopic ellipsometer using best-local-minimum-calculation (BLMC), said method comprising:
    a spectrum measurement step wherein incident light is cast onto a thin film on a substrate which is to be measured while changing the wavelength of the incident light as a parameter in order to obtain the $\Psi_E(\lambda_i)$ and $\Delta_E(\lambda_i)$ spectrums for each wavelength $\lambda_1$, which represent the change in polarization between the incident light and the reflected light;
    a step for forming models of said film structure, wherein a thin film on a substrate is formed with microscopic non-uniformity, or is formed of a mixture of several materials, with the complex refractive index ($N_0$ ($n_0$, $k_0$)) of said substrate and the complex refractive index (N (n, k)) of said film, assumed based upon several dispersion formulas or reference data, which are used for Effective Medium Approximation (EMA);
    a step for assuming a plurality of film thicknesses within a plausible range, a plurality of volume fractions within a plausible range obtained based upon said dispersion formulas which have been employed in forming said models, and a plurality of incident angles within a plausible range;

a step for performing fitting for the parameters of the dispersion formula (DSP) based upon combinations of said incident angle, said film thickness, and said volume fraction;

a first analyzing step for selecting fitting results obtained based upon a model formed of a combination of said film thickness, said incident angle, and said volume fraction, which exhibits the minimal difference between the $\Psi_M(\lambda_i)$ and $\Delta_M(\lambda_i)$ obtained by said fitting and said measured $\Psi_E(\lambda_i)$ and $\Delta_E(\lambda_i)$; and a second analyzing step for performing fitting for the film thickness, the volume fraction and said dispersion formula with the incident angle obtained in said first analyzing step being fixed.

4. An extremely-thin-film measurement and thin-film measurement method for analyzing spectroscopic data acquired from a spectroscopic ellipsometer using best-local-minimum-calculation (BLMC), said method comprising:

a spectrum measurement step wherein incident light is cast onto a thin film on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light;

a step for assuming a plurality of measurement conditions ($Z_j$) in a plausible range and performing processing from said second step of claim 1 for forming models of a film structure, to said second step, for each ($Z_j$); and a third analyzing step for selecting fitting results, of which said parameters of said dispersion formula and said volume fraction are within predetermined ranges, exhibiting the minimal mean square error ($\chi^2$), from the fitting results obtained based upon said plurality of measurement conditions ($Z_i$).

5. An extremely-thin-film double-layer-structure measurement method for analyzing spectroscopic data acquired from a spectroscopic ellipsometer, said method comprising:

a spectrum measurement stage wherein incident light is cast onto an extremely-thin-film double-layer structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light;

a first analyzing stage which includes:

a first analyzing step of said first analyzing stage for forming several models of said extremely-thin-film double-layer structure on said substrate based upon the complex refractive index ($N_0$ ($n_0$, $k_0$)) of said substrate, the complex refractive indexes ($N_1$ ($n_1$, $k_1$)) and ($N_2$ ($n_2$, $k_2$)) of materials (Mat 1, Mat 2) of said thin films in plausible ranges, and the film thicknesses ($d_1$, $d_2$) in plausible ranges;

a second analyzing step of said first analyzing stage for performing fitting for said measured spectrums for each model; and a third analyzing step of said first analyzing stage for selecting fitting results obtained based upon a model which exhibits the minimal mean square error ($\chi^2$), or a model with said film thicknesses being within predetermined ranges, which exhibits the minimal mean square error ($\chi^2$), from the fitting results obtained based upon said several models;

a second analyzing stage which includes:

a first analyzing step of said second analyzing stage for setting initial values of a new model to the fitting results obtained in said first analyzing stage;

a second analyzing step of said second analyzing stage for performing fitting for multiple models with a film-thickness combination as a parameter around and at the film-thickness combination serving as the median, using best-local-minimum-calculation (BLMC); and a third analyzing step of said second analyzing stage for selecting a model which exhibits the minimal mean square error ($\chi^2$), or a model with said film thicknesses, the parameters of the dispersion formula, and the incident angle, being within predetermined ranges, which exhibits the minimal mean square error ($\chi^2$);

a third analyzing stage which includes:

a first analyzing step of said third analyzing stage for performing the final fitting based upon the fitting results obtained in said second analyzing stage;

a second analyzing step of said third analyzing stage for confirming said fitting results obtained in said first analyzing step of said third analyzing stage; and a third analyzing step of said third analyzing stage for storing said obtained fitting results.

6. An extremely-thin-film double-layer-structure measurement method for analyzing spectroscopic data acquired from a spectroscopic ellipsometer according to claim 5, wherein in said second analyzing step of said second analyzing stage, fitting is performed using BLMC for materials formed of said double-layer structure in order of uncertainty of the optical constants thereof.

7. An extremely-thin-film double-layer-structure measurement method for analyzing spectroscopic data acquired from a spectroscopic ellipsometer according to claim 5, further comprising:

a step for forming multiple models with the film thickness obtained in said third analyzing step of said first analyzing stage, of which the optical constants are more reliable than the other, as a parameter around and at the film thickness obtained in a range of a few percents to a few ten percents; and a step for performing BLMC described in said second and third analyzing steps of said second analyzing stage for the other layer for each model.

8. An extremely-thin-film double-layer-structure measurement method for analyzing spectroscopic data acquired from a spectroscopic ellipsometer, said method comprising:

a spectrum measurement stage wherein incident light is cast onto an extremely-thin-film double-layer-structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light;

a first analyzing stage which includes:

a first analyzing step of said first analyzing stage for forming several models of one of the first and second layers, which is formed with non-uniformity or non-continuity, or is formed of a mixture of several materials, with the complex refractive index ($N_0$ ($n_0$, $k_0$)) of said substrate thereof, the complex refractive indexes ($N_1$ ($n_1$, $k_1$)) and ($N_2$ ($n_2$, $k_2$)) of the materials (Mat 1, Mat 2) forming said thin films in plausible ranges, the volume fractions ($Vf_1$, $Vf_2$) in plausible ranges, and the film thicknesses ($d_1$, $d_2$) in plausible ranges, using Effective Medium Approximation (EMA);

a second analyzing step of said first analyzing stage for performing fitting for said measured spectrums for each model; and a third analyzing step of said first analyzing stage for selecting fitting results obtained based upon a model which exhibits the minimal mean square error ($\chi^2$), or a model with said film thicknesses and said volume fractions being within predetermined ranges, which exhibits the minimal mean square error ($\chi^2$), from the fitting results obtained based upon said several models;

a second analyzing stage which includes:

a first analyzing step of said second analyzing stage for forming new models with the initial values based upon the fitting results obtained in said first analyzing stage, with the film thickness, wherein the corresponding parameters of the dispersion formula are less known than the other, as a parameter around the value obtained said third analyzing step of said first analyzing stage in a range of a plurality of film thicknesses within a plausible range, with the film thickness of the other layer as a parameter around the value obtained in said third analyzing step of said first analyzing stage in a range of a plurality of film thicknesses within a plausible range, and with the volume fraction as a parameter around the value obtained in said third analyzing step of said first analyzing stage in a range of a plurality of volume fractions within a plausible range;

a second analyzing step of said second analyzing stage for performing best-local-minimum-calculation (BLMC) for the parameters of said layer, wherein the parameters of the dispersion formula are less known than the other, of said models obtained in said first analyzing step of said second analyzing stage; and a third analyzing step of said second analyzing stage for selecting a model which exhibits the minimal mean square error ($\chi^2$), or a model with the film thicknesses, the parameters of the dispersion formula, and the incident angle, being within predetermined ranges, which exhibits the minimal mean square error ($\chi^2$), from the fitting results obtained in said second analyzing step of said second analyzing stage;

a third analyzing stage which includes:

a first analyzing step of said third analyzing stage for performing fitting for said film thicknesses of both thin films, said volume fraction, and said parameters of the dispersion formula, or performing fitting for said film thicknesses of both thin films and said volume fraction, based upon the fitting results obtained in said second analyzing stage;

a second analyzing step of said third analyzing stage for confirming said fitting results obtained in said first analyzing step of said third analyzing stage; and a third analyzing step of said third analyzing stage for storing said obtained fitting results.

9. An extremely-thin-film double-layer-structure measurement method for analyzing spectroscopic data acquired from a spectroscopic ellipsometer according to claim 5, further comprising:

a spectrum measurement stage wherein incident light is cast onto an extremely-thin-film double-layer-structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light;

a step for assuming a plurality of measurement conditions (Zi) in a plausible range, and performing processing of said first analyzing stage or first through third analyzing step of said second analyzing stage for each assumed measurement condition (Zi); and a fourth analyzing step of said first or second analyzing stage for selecting fitting results, which exhibit the minimal mean square error ($\chi^2$), or the parameters of the dispersion formula, and the volume fraction, are within a predetermined range, and which exhibit the minimal mean square error ($\chi^2$) which are selected from the fitting results obtained in said analyzing step.

10. An extremely-thin-film double-layer-structure measurement method for analyzing spectroscopic data acquired from a spectroscopic ellipsometer according to claim 5, wherein in each of said steps for selecting the results which exhibit the least difference, described in said first, second and third analyzing stage, the mean square error ($\chi^2$) are obtained between the fitting results and the measured values, and the fitting results which exhibit the minimal mean square error ($\chi^2$), or the fitting results, of which the film thicknesses, the parameters of the dispersion formula, the volume fraction, and the change in the incident angle, are within predetermined ranges, and which exhibit the minimal mean square error ($\chi^2$), are selected.

11. A thin-film triple-layer-structure measurement method for analyzing spectroscopic data acquired from a spectroscopic ellipsometer, said method comprising: a spectroscopic measurement phase for obtaining measured data using a spectroscopic ellipsometer;

a first analyzing phase for forming an initial model of a thin-film triple-layer-structure;

a second analyzing phase which includes:

a first analyzing stage of said second analyzing phase for determining unknown parameters of the layer of interest forming said thin-film triple-layer-structure, using extended best-local-minimum-calculation (EBLMC); and a second analyzing stage of said second analyzing phase for determining parameters of the other layers with said parameters determined in said first analyzing stage of said second analyzing phase being fixed, using EBLMC.

12. A thin-film triple-layer-structure measurement method for analyzing spectroscopic data acquired from a spectroscopic ellipsometer, said method comprising:

a spectroscopic measurement phase for obtaining measured data using a spectroscopic ellipsometer;

a first analyzing phase for forming an initial model of a thin-film triple-layer-structure;

a second analyzing phase which includes:

a first analyzing stage of said second analyzing phase for determining unknown parameters of the layer of interest forming said thin-film triple-layer-structure, using extended best-local-minimum-calculation (EBLMC); and a second analyzing stage of said second analyzing phase for determining parameters of the other layers with said parameters determined in said first analyzing stage of said second analyzing phase being fixed, using EBLMC;
a third analyzing phase which includes:
   a first analyzing stage of said third analyzing phase for performing the final fitting for the model obtained in said second analyzing phase;
   a second analyzing stage of said third analyzing phase for confirming the fitting results obtained in said first analyzing stage of said third analyzing phase; and
   a third analyzing stage of said third analyzing phase for storing the fitting results obtained in said second analyzing stage of said third analyzing phase.

13. A thin-film n-layer-structure measurement method for analyzing spectroscopic data acquired from a spectroscopic ellipsometer, said method comprising:
   a spectroscopic measurement phase for obtaining measured data using a spectroscopic ellipsometer;
   a first analyzing phase for forming an initial model of a thin-film n-layer-structure; and
   a second analyzing phase for determining unknown parameters of the layer of interest forming the n-layer structure based upon said initial model which represents said thin-film n-layer-structure, using extended best-local-minimum-calculation (EBLMC).

14. A thin-film n-layer-structure measurement method for analyzing spectroscopic data acquired from a spectroscopic ellipsometer, said method comprising:
   a spectroscopic measurement phase for obtaining measured data using a spectroscopic ellipsometer;
   a first analyzing phase for forming an initial model of a thin-film n-layer-structure;
   a second analyzing phase for determining unknown parameters of the layer of interest forming the n-layer structure based upon said initial model, using extended best-local-minimum-calculation (EBLMC);
   a third analyzing phase which includes:
      a first analyzing stage of said third analyzing phase for performing the final fitting for the model obtained in said second analyzing phase;
      a second analyzing stage of said third analyzing phase for confirming the fitting results obtained in said first analyzing stage; and
      a third analyzing stage of said third analyzing phase for storing the fitting results obtained in said second analyzing stage.

15. A thin-film triple-layer-structure measurement or thin-film multi-layer-structure measurement method for analyzing spectroscopic data acquired from a spectroscopic ellipsometer according to claim 11, wherein analysis is made with unknown parameters as the film thicknesses, the optical constants of unknown materials or the volume fractions.

16. A thin-film triple-layer-structure measurement or thin-film multi-layer-structure measurement method for analyzing spectroscopic data acquired from a spectroscopic ellipsometer according to claim 11, wherein said spectroscopic measurement phase includes:
   a spectrum measurement step wherein incident light is cast onto a thin-film triple-layer structure or a thin-film multi-layer structure on a substrate which is to be measured while changing the wavelength of the incident light as a parameter in order to obtain the $\Psi_E(\lambda_i)$ and $\Delta_E(\lambda^1)$ spectra for each wavelength $\lambda_i$, which represent the change in polarization between the incident light and the reflected light; and
   a storage step for storing the data obtained in said measured step.

17. A thin-film triple-layer-structure measurement or thin-film multi-layer-structure measurement method for analyzing spectroscopic data acquired from a spectroscopic ellipsometer according to claim 11, wherein in said first analyzing phase, the single Best First Approximation Model (BFAM) is selected from a plurality of models by fitting, or a model is assumed based upon known data, as said initial model,
   and wherein in a case of employing said BFAM, said first analyzing phase includes:
      a first analyzing step of said first analyzing phase for forming a plurality of models within a plausible range;
      a second analyzing step of said first analyzing phase for performing fitting with regard to the film thicknesses, the volume fractions, and the incident angles, based upon said plurality of models; and
      a third analyzing step of said first analyzing phase for selecting a model which exhibits the minimal mean square error ($\chi^2$), or a model, of which said film thicknesses, said volume fractions, and said incident angles, are within predetermined ranges, and which exhibit the minimal mean square error ($\chi^2$), from the fitting results obtained in said second analyzing step of said first analyzing phase.

18. A thin-film triple-layer-structure measurement or thin-film multi-layer-structure measurement method for analyzing spectroscopic data acquired from a spectroscopic ellipsometer according to claim 11, wherein said first analyzing stage of said second analyzing phase includes:
   a first-first analyzing step of said second analyzing phase for replacing the optical constants of the layer of interest with a single dispersion formula, which is the least known in said thin-film triple-layer structure or thin-film n-layer structure, in said determined initial model;
   a first-second analyzing step of said second analyzing phase for forming a plurality of models based upon said initial model with the film thicknesses, the volume fractions, or the like, of desired layers other than said layer of interest (the number of layers is 1 through (n−1)), as parameters, and performing EBLMC for said layer of interest based upon each model;
   a first-third analyzing step of said second analyzing phase for selecting a model which exhibit the minimal mean square error ($\chi^2$), or a model, of which said film thicknesses, said volume fractions, said parameters of the dispersion formula, and said incident angle, are within predetermined ranges, and which exhibit the minimal mean square error ($\chi^2$), from the fitting results using EBLMC, obtained in said first-second analyzing step of said second analyzing phase.

19. A thin-film triple-layer-structure measurement or thin-film multi-layer-structure measurement method for analyzing spectroscopic data acquired from a spectroscopic ellipsometer according to claim 18, wherein in each of second analyzing stage of said second analyzing phase through $t^{th}$ analyzing stage of said second analyzing phase, the same steps as said first-first analyzing step of said second analyzing phase through first analyzing step of said second analyzing phase are performed, making an assumption that the optical constants of the layer of interest obtained in the previous stage are almost known.

20. A thin-film triple-layer-structure measurement or thin-film multi-layer-structure measurement method for analyzing spectroscopic data acquired from a spectroscopic ellipsometer according to claim 11, wherein in said second analyzing phase, EBLMC is performed for the materials forming said triple-layer structure or n-layer structure in order of uncertainty of the optical constants of said materials, and wherein said EBLMC is performed for at least one to t times, regardless of the number of the layers in said structure.

21. A thin-film triple-layer-structure measurement or thin-film multi-layer-structure measurement method for analyzing spectroscopic data acquired from a spectroscopic ellipsometer according to claim 11, wherein in said second analyzing phase, in the event that the fitting results with the minimal mean square error ($\chi^2$) do not exhibit said film thicknesses, said parameters of the dispersion formula, said volume fractions, and said incident angle, within predetermined ranges, said second analyzing phase is repeated with a certain number of iterations.

22. A thin-film triple-layer-structure measurement or thin-film multi-layer-structure measurement method for analyzing spectroscopic data acquired from a spectroscopic ellipsometer according to claim 12, wherein in said third analyzing phase, the final fitting is performed for desired parameters of the model obtained said second analyzing phase, confirmation is made for the fitting results obtained in said final fitting, and said fitting results are stored.

23. A thin-film triple-layer-structure measurement or thin-film multi-layer-structure measurement method for analyzing spectroscopic data acquired from a spectroscopic ellipsometer according to claim 12, wherein in the event that confirmation is made in said second analyzing step of said third analyzing phase that the fitting results with the minimal mean square error ($\chi^2$) obtained in said first analyzing step of said third analyzing phase are not within predetermined ranges, the flow returns to said first analyzing phase, and analysis is made again.

24. A thin-film triple-layer-structure measurement or thin-film multi-layer-structure measurement method for analyzing spectroscopic data acquired from a spectroscopic ellipsometer according to claim 11, wherein said first analyzing stage of said second analyzing phase includes:
a first-first analyzing step of said second analyzing phase wherein in the event that the layer of interest cannot be represented by a single dispersion formula, Effective Medium Approximation (EMA) is performed making an assumption that said layer of interest is formed of a mixture of several materials, and at least one material forming" said layer of interest is represented by a dispersion formula; and
a first-second analyzing step of said second analyzing phase for forming multiple models with film thicknesses or volume fractions of desired layers 1 through (n−1) (n denotes the number of layers of said structure) other than said layer of interest, as parameters and performing EBLMC for said layer of interest for each model while changing the volume fraction thereof as a parameter.

25. A thin-film triple-layer-structure measurement or thin-film multi-layer-structure measurement method for analyzing spectroscopic data acquired from a spectroscopic ellipsometer according to claim 11, further comprising:
a spectroscopic measurement phase wherein incident light is cast onto a triple-layer-structure or multi-layer-structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the charge in polarization between the incident light and the reflected light;
an analyzing step for assuming a plurality of measurement conditions (Zi) in a plausible range and performing processing from said first analyzing step or first analyzing step of said first analyzing phase through $t^{th}$-third analyzing step of said second analyzing phase for each assumed measurement condition (Zi); and
a fourth analyzing step of said first analyzing phase or $t^{th}$-fourth analyzing step of said second analyzing phase for selecting fitting results, which exhibit the minimal mean square error ($\chi^2$), or the parameters of the dispersion formula, the volume fraction, and the incident angle, are within a predetermined range, and which exhibit the minimal mean square error ($\chi^2$) which are selected from the fitting results obtained in said analyzing step.

26. A thin-film triple-layer-structure measurement or thin-film multi-layer-structure measurement method for analyzing spectroscopic data acquired from a spectroscopic ellipsometer according to claim 12, wherein in each of said steps for selecting the results which exhibit the least difference, described in said first, second and third analyzing phases, the mean square error ($\chi^2$) are obtained between the fitting results and the measured values, and the fitting results which exhibit the minimal mean square error ($\chi^2$), or the fitting results, of which the film thicknesses, the parameters of the dispersion formula, the volume fraction, and the change in the incident angle, are within predetermined ranges, and which exhibit the minimal mean square error ($\chi^2$), are selected.

27. A thin-film triple-layer-structure measurement or thin-film multi-layer-structure measurement method for analyzing spectroscopic data acquired from a spectroscopic ellipsometer according to claim 13, wherein analysis is made with unknown parameters as the film thicknesses, the optical constants of unknown materials or the volume fractions.

28. A thin-film triple-layer-structure measurement or thin-film multi-layer-structure measurement method for analyzing spectroscopic data acquired from a spectroscopic ellipsometer according to claim 13, wherein said spectroscopic measurement phase includes: a spectrum measurement step wherein incident light is cast onto a thin-film triple-layer structure or a thin-film multi-layer structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light; and a storage step for storing the data obtained in said measured step.

29. A thin-film triple-layer-structure measurement or thin-film multi-layer-structure measurement method for analyzing spectroscopic data acquired from a spectroscopic ellipsometer according to claim 13, wherein in said first analyzing phase, the single Best First Approximation Model (BFAM) is selected from a plurality of models by fitting, or a model is assumed based upon known data, as said initial model,
and wherein in a case of employing said BFAM, said first analyzing phase includes:
a first analyzing step of said first analyzing phase for forming a plurality of models within a plausible range;
a second analyzing step of said first analyzing phase for performing fitting with regard to the film thicknesses, the volume fractions, and the incident angles, based upon said plurality of models; and
a third analyzing step of said first analyzing phase for selecting a model which exhibits the minimal mean square error ($\chi^2$), or a model, of which said film thicknesses, said volume fractions, and said incident angles, are within predetermined ranges, and which exhibit the minimal mean square error ($\chi^2$), from the fitting results obtained in said second analyzing step of said first analyzing phase.

30. A thin-film triple-layer-structure measurement or thin-film multi-layer-structure measurement method for analyzing spectroscopic data acquired from a spectroscopic ellipsometer according to claim 13, wherein said first analyzing stage of said second analyzing phase includes:

a first-first analyzing step of said second analyzing phase for replacing the optical constants of the layer of interest with a single dispersion formula, which is the least known in said thin-film triple-layer structure or thin-film n-layer structure, in said determined initial model;

a first-second analyzing step of said second analyzing phase for forming a plurality of models based upon said initial model with the film thicknesses, the volume fractions, or the like, of desired layers other than said layer of interest (the number of layers is 1 through (n−1)), as parameters, and performing EBLMC for said layer of interest based upon each model;

a first-third analyzing step of said second analyzing phase for selecting a model which exhibit the minimal mean square error ($\chi^2$), or a model, of which said film thicknesses, said volume fractions, said parameters of the dispersion formula, and said incident angle, are within predetermined ranges, and which exhibit the minimal mean square error ($\chi^2$), from the fitting results using EBLMC, obtained in said first-second analyzing step of said second analyzing phase.

31. A thin-film triple-layer-structure measurement or thin-film multi-layer-structure measurement method for analyzing spectroscopic data acquired from a spectroscopic ellipsometer according to claim 14, wherein analysis is made with unknown parameters as the film thicknesses, the optical constants of unknown materials or the volume fractions.

32. A thin-film triple-layer-structure measurement or thin-film multi-layer-structure measurement method for analyzing spectroscopic data acquired from a spectroscopic ellipsometer according to claim 14, wherein said spectroscopic measurement phase includes: a spectrum measurement step wherein incident light is cast onto a thin-film triple-layer structure or a thin-film multi-layer structure on a substrate which is to be measured while changing the wavelength of the incident light as a parameter in order to obtain the $\Psi_E(\lambda_i)$ and $\Delta_E(\lambda_i)$ spectrums for each wavelength $\lambda_i$, which represent the change in polarization between the incident light and the reflected light; and a storage step for storing the data obtained in said measured step.

33. A thin-film triple-layer-structure measurement or thin-film multi-layer-structure measurement method for analyzing spectroscopic data acquired from a spectroscopic ellipsometer according to claim 14, wherein in said first analyzing phase, the single Best First Approximation Model (BFAM) is selected from a plurality of models by fitting, or a model is assumed based upon known data, as said initial model, and wherein in a case of employing said BFAM, said first analyzing phase includes:

a first analyzing step of said first analyzing phase for forming a plurality of models within a plausible range;

a second analyzing step of said first analyzing phase for performing fitting with regard to the film thicknesses, the volume fractions, and the incident angles, based upon said plurality of models; and a third analyzing step of said first analyzing phase for selecting a model which exhibits the minimal mean square error ($\chi^2$), or a model, of which said film thicknesses, said volume fractions, and said incident angles, are within predetermined ranges, and which exhibit the minimal mean square error ($\chi^2$), from the fitting results obtained in said second analyzing step of said first analyzing phase.

34. A thin-film triple-layer-structure measurement or thin-film multi-layer-structure measurement method for analyzing spectroscopic data acquired from a spectroscopic ellipsometer according to claim 14, wherein said first analyzing stage of said second analyzing phase includes:

a first-first analyzing step of said second analyzing phase for replacing the optical constants of the layer of interest with a single dispersion formula, which is the least known in said thin-film triple-layer structure or thin-film n-layer structure, in said determined initial model;

a first-second analyzing step of said second analyzing phase for forming a plurality of models based upon said initial model with the film thicknesses, the volume fractions, or the like, of desired layers other than said layer of interest (the number of layers is 1 through (n−1)), as parameters, and performing EBLMC for said layer of interest based upon each model;

a first-third analyzing step of said second analyzing phase for selecting a model which exhibit the minimal mean square error ($\chi^2$), or a model, of which said film thicknesses, said volume fractions, said parameters of the dispersion formula, and said incident angle, are within predetermined ranges, and which exhibit the minimal mean square error ($\chi^2$), from the fitting results using EBLMC, obtained in said first-second analyzing step of said second analyzing phase.

* * * * *